US008932447B2

(12) United States Patent
Heller et al.

(10) Patent No.: US 8,932,447 B2
(45) Date of Patent: Jan. 13, 2015

(54) EX-VIVO MULTI-DIMENSIONAL SYSTEM FOR THE SEPARATION AND ISOLATION OF CELLS, VESICLES, NANOPARTICLES, AND BIOMARKERS

(71) Applicant: The Regents of the University of California, Oakland, CA (US)

(72) Inventors: Michael Heller, San Diego, CA (US); Benjamin Sullivan, San Diego, CA (US); Rajaram Krishnan, La Jolla, CA (US); Dennis Carson, La Jolla, CA (US); Sadik C. Esener, Solana Beach, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/063,884

(22) Filed: Oct. 25, 2013

(65) Prior Publication Data

US 2014/0048417 A1     Feb. 20, 2014

Related U.S. Application Data

(62) Division of application No. 12/936,147, filed as application No. PCT/US2009/039565 on Apr. 3, 2009.

(60) Provisional application No. 61/042,228, filed on Apr. 3, 2008.

(51) Int. Cl.
*B03C 5/02*     (2006.01)
*B03C 5/00*     (2006.01)
(Continued)

(52) U.S. Cl.
CPC .............. *B03C 5/005* (2013.01); *G01N 27/447* (2013.01); *G01N 33/491* (2013.01); *G01N 30/0005* (2013.01)
USPC .......................................... 204/547; 204/643

(58) Field of Classification Search
CPC ................. B03C 5/005–5/028; G01N 27/447; G01N 33/491; G01N 30/005
USPC .................... 204/547, 643, 450, 600
See application file for complete search history.

(56) References Cited

U.S. PATENT DOCUMENTS 4,661,451 A * 4/1987 Hansen ......................... 435/174
5,632,957 A   5/1997 Heller
(Continued)

FOREIGN PATENT DOCUMENTS

| CN | 1337580 | 2/2002 |
| CN | 1348100 | 5/2002 |

(Continued)

OTHER PUBLICATIONS

Gunter Fuhr, Henning Glasser, Torsten Muller, Thomas Schnelle, Cell manipulation and cultivation under a.c. electric field influence in highly conductive culture media, Biochimica et Biophysica Acta 1201, pp. 353-360 (1994).*
(Continued)

*Primary Examiner* — J. Christopher Ball
*Assistant Examiner* — Maris R Kessel
(74) *Attorney, Agent, or Firm* — Fish & Richardson P.C.

(57) ABSTRACT

Devices and techniques are described that involve a combination of multidimensional electrokinetic, dielectrophoretic, electrophoretic and fluidic forces and effects for separating cells, nanovesicles, nanoparticulates and biomarkers (DNA, RNA, antibodies, proteins) in high conductance (ionic) strength biological samples and buffers. In disclosed embodiments, a combination of continuous and/or pulsed dielectrophoretic (DEP) forces, continuous and/or pulsed field DC electrophoretic forces, microelectrophoresis and controlled fluidics are utilized with arrays of electrodes. In particular, the use of chambered DEP devices and of a properly scaled relatively larger electrode array devices that combines fluid, electrophoretic and DEP forces enables both larger and/or clinically relevant volumes of blood, serum, plasma or other samples to be more directly, rapidly and efficiently analyzed. The invention enables the creation of "seamless" sample-to-answer diagnostic systems and devices. The devices and techniques described can also carry out the assisted self-assembly of molecules, polymers, nanocomponents and mesoscale entities into three dimensional higher order structures.

10 Claims, 28 Drawing Sheets

(51) Int. Cl.
G01N 27/447 (2006.01)
G01N 33/49 (2006.01)
G01N 30/00 (2006.01)

(56) References Cited

U.S. PATENT DOCUMENTS

| | | | |
|---|---|---|---|
| 6,280,590 | B1 | 8/2001 | Cheng et al. |
| 6,403,367 | B1 | 6/2002 | Cheng |
| 6,749,736 | B1 | 6/2004 | Fuhr |
| 6,824,664 | B1 | 11/2004 | Austin |
| 7,105,081 | B2 | 9/2006 | Gascoyne |
| 2001/0045359 | A1* | 11/2001 | Cheng et al. ............. 204/547 |
| 2002/0036142 | A1* | 3/2002 | Gascoyne et al. ........ 204/547 |
| 2003/0146100 | A1 | 8/2003 | Huang et al. |
| 2004/0011651 | A1* | 1/2004 | Becker et al. ............. 204/547 |
| 2006/0102482 | A1* | 5/2006 | Auerswald et al. ........ 204/547 |
| 2006/0289341 | A1 | 12/2006 | Muller et al. |
| 2007/0095669 | A1* | 5/2007 | Lau et al. ................. 204/547 |
| 2007/0125650 | A1 | 6/2007 | Scurati et al. |
| 2007/0131554 | A1 | 6/2007 | Yu et al. |
| 2007/0240495 | A1 | 10/2007 | Hirahara |
| 2007/0284254 | A1 | 12/2007 | Cho |
| 2011/0108422 | A1 | 5/2011 | Heller et al. |

FOREIGN PATENT DOCUMENTS

| | | |
|---|---|---|
| EP | 1775589 | 4/2007 |
| WO | WO 99/38612 | 8/1999 |
| WO | WO 01/96025 | 12/2001 |
| WO | WO 2007/107910 | 9/2007 |

OTHER PUBLICATIONS

PCT/US2009/039565 International Search Report dated Dec. 23, 2009, 3 pages.
PCT/US2009/039565 International Preliminary Report on Patentability and Written Opinion dated Dec. 23, 2009, 9 pages.
Extended European Search Report for EP Application No. 09755505.6, dated Jun. 18, 2012, 11 pages.
Communication pursuant to Rules 70(2) and 70a(2) EPC in EP Application No. 09755505.6, dated Jul. 5, 2012, 1 page.
Asbury et al., "Trapping of DNA by dielectrophoresis," Electrophoresis, 23:2658-2666, 2002.
Asbury et al., "Trapping of DNA in Nonuniform Oscillating Electric Fields," Biophys J., 74:1024-1030, 1998.
Becker et al., "The removal of human leukemia cells from blood using interdigitated microelectrodes," J Phys. D: Appl. Phys., 27:2659-2662, 1994.
Becker et al., "Separation of Human Breast Cancer Cells From Blood by Differential Dielectric Affinity," Proceedings of the National Academy of Sciences, 92:860-864, 1995.
Cheng et al., "Isolation of Cultured Cerivcal Carcinoma Cells Mixed with Peripheral Blood Cells on a Bioelectronic Chip", Analytical Chemistry, 70(11):2321-2326, 1998.
Cheng et al., "Preparation and Hybridization Analysis of DNAIA from *E. coli* on 15 Microfabricated Bioelectronic Chips", Nature Biotechnology, 16:541-546, 1998.
Gautschi et al., "Circulating deoxyribonucleic Acid as prognostic marker in non-small-cell lung cancer patients undergoing chemotherapy," J Clin Oneol., 22:4157-64, 2004.
Goodard et al., Handbook of Nanoscience, 2nd edition, ch 16, p. 5-8.
Green et al., "Ac electrokinetics: a survey of sub-micrometre paricle dynamics," J. Phys. D: Appl. Phys., 33:632-641, 2000.
Higuchi, "Chromosomal DNA fragmentation inapoptosis and necrosis induced by oxidative stress," Biochem Pharacol., 66: 1527-35, 2003.
Higuchi and Matsukawa, "Appearance of 1-2 Mbp giant DNA fragments as an early common response leading to cell death induced by various substances that cause oxidative stress," Free Radical Biology & Medicine, 23:90-99, 1997.
Holzel et al., Trapping Single Molecules by Dielectrophoresis. Phys. Rev. Left., 95:128102 (2005).
Huang et al., "Electric Manipulation ofBioparicl es and Macromolecules on Microfabricated Electrodes", Analytical Chemistry 2001, 73:1549-59.
Huang et al., "Dielectrophoretic Cell Separation 20 and Gene Expression Profiling on Microelectronic Chip Arrays", Analytical Chem. 2002, 74:3362-71.
Hughes and Morgan, "Dielectrophoretic Characterization and Separation of Antibody-Coated Submicrometer Latex Spheres," Anal Chem., 1999, 71:3441-3445.
Hughes et al., "Dielectrophoretic manipulation and characterization of herpes simplex virus-1 capsids," Eur Biophys J, 2001, 30:268-272.
Hughes, "Strategies for dielectrophoretic separation in laboratory-on-a-chip sytems," Electrophoresis, 2002, 23:2569-2582.
Krishnan et al., "Alternating current electrokinetic separation and detection of DNA nanoparticles in high-conductance solutions," Electrophoresis, 2008, 29:1765-1774.
Krishnan et al., "Interaction of nanoparticles at the DEP microelectrode interface under high conductance conditions," Electrochem Commun., 2009, 11:1661-1666.
Morgan et al., "Separation of Sub micron Bioparticles by Dielectrophoresis" Biophysical J., 77:516-525, 1999.
Pethig, "Dielectrophoresis: Using Inhomogeneous AC Electrical Fields to Separate and Manipulate Cells," CRC Critical Reviews in Biotechnology, CRC Press, Boca Raton, FL, US, 16(4):331-348, Jan. 1, 1996.
Ramos et al., "Ac electrokinetics: a review of forces in microelectrode structures," J Phys. D: Appl. Phys., 31:2338-2353, 1998.
Stephens et al., "The dielectrophoresis enrichment of CD34+ cells from peripheral blood stern cell harvests," Bone Marrow Transplant, 18:777-82, 1996.
Stroun et al., "Isolation and characterization of DNA from the plasma of cancer patients," Eur J Cancer Clin Oneol., 23:707-712, 1987.
Tong and Lo, "Diagnostic developments involving cell-free (circulating) nucleic acids," Clinica Chimica Acta., 363:187-96, 2006.
Tuukanen et al., "Carbon nanotubes as electrodes for dielectrophoresis of DNA," Nano Letters, 6:1339-1343, 2006.
Washizu et al., "Applications of electrostatic stretch-and-positioning of DNA," Industry Applications, IEEE Transactions on. 31:447-456, 1995.
Washizu and Kurosawa, "Electrostatic manipulation of DNA in microfabricated structures," Industry Applications, IEEE Transactions on. 26:1165-1172; 1990.
Wu TL et al., "Cell-free DNA: measurement in varous carcinomas and establishment of normal reference range," Clin ChimActa., 21:77-87, 2002.
Ziegler et al., "Circulating DNA: a new diagnostic gold mine?" Cancer Treat Rev., 5:255-71, 2002.
Office Action in Japanese Application No. 2013-119141, dated Jun. 3, 2014, 2 pages (English Translation).
Office Action in Chinese Application No. 201310248023.X, dated Aug. 20, 2014, 12 pages (with English translation).

\* cited by examiner

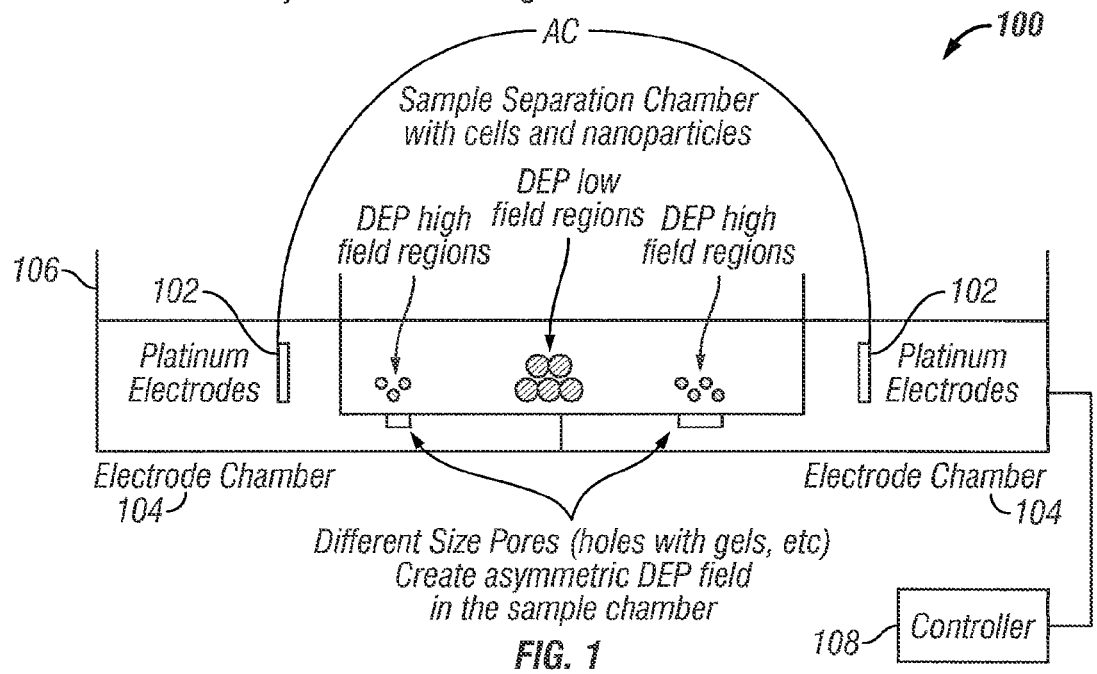
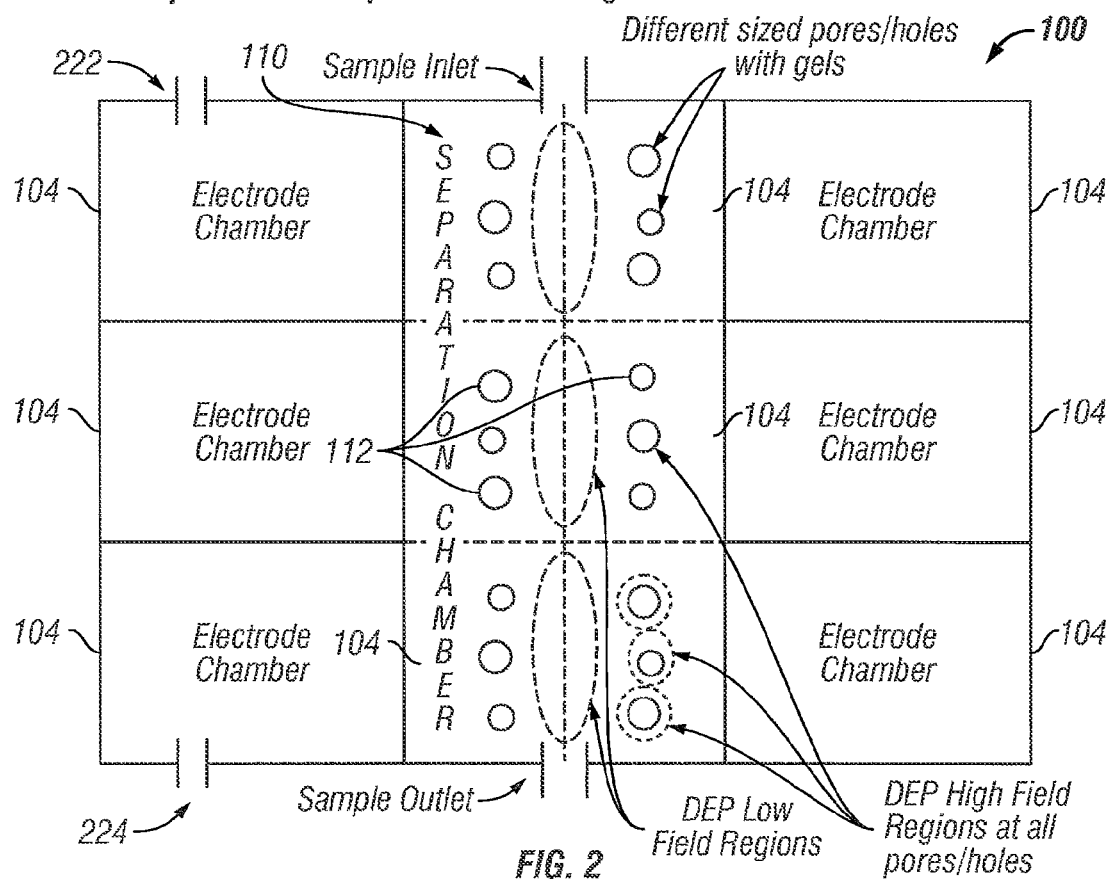

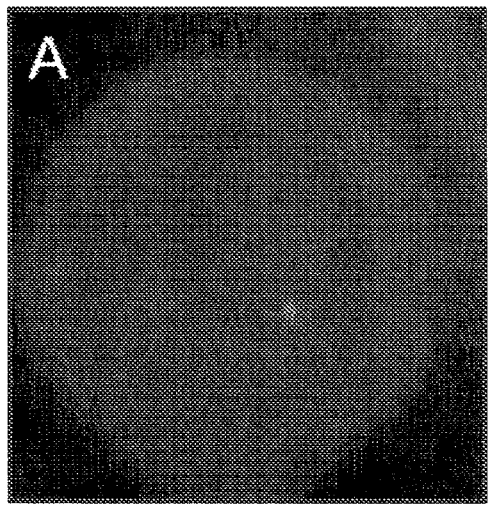
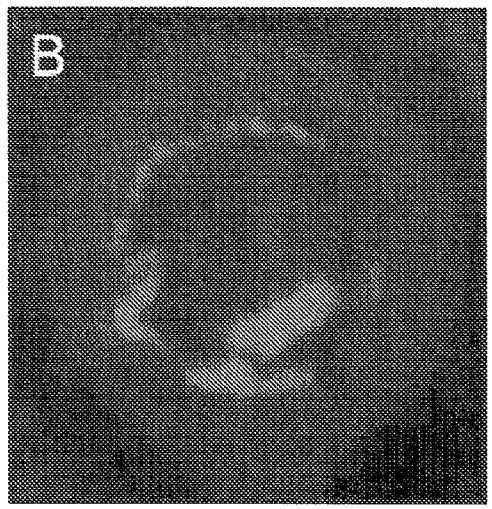
*FIG. 26A*  *FIG. 26B*
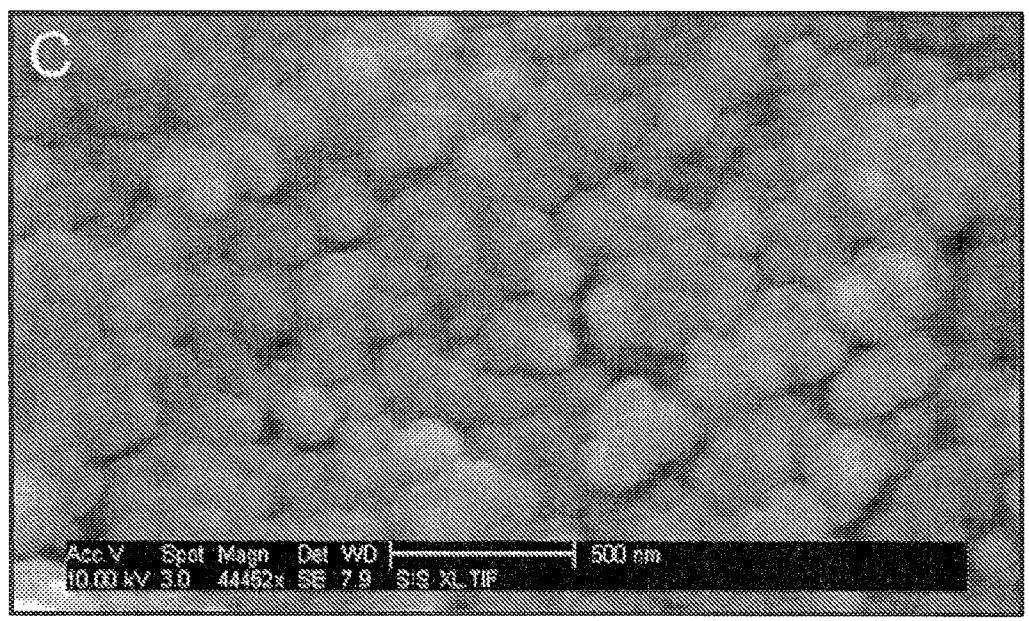
*FIG. 26C*

*Seamless Sample to Answer for Direct Analysis of Blood, Plasma, Serum and Other Biological Samples*
*Step 1 - Blood sample applied to the DEP device*

*Step 2 - The DEP field is applied (5 minutes) Cells move to low field regions and hmw DNA biomarkers into high field regions*

*Step 3 - Fluidic wash (1 minute)*
*Blood cells are removed while hmw-DNA biomarkers remain concentrated in high field regions*

DEP Separation/Detection Array Device

*Step 4 - Add Fluorescent DNA/RNA Stain and Wash*

Step 5 - Detect and Quantitate Fluorescent DNA/RNA
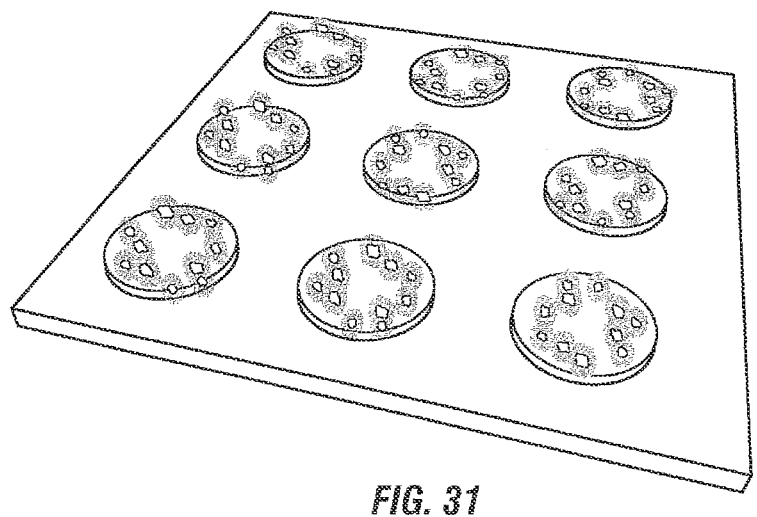
FIG. 31
Other Biomarkers and Analytes
Cells/ Bacteria/Virus     Cellular Nanoparticulates (CNPs)     hmw DNA/RNA 
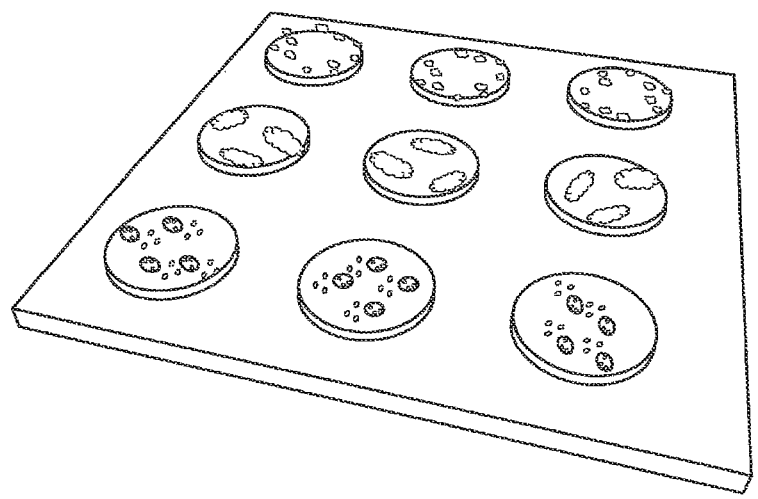
FIG. 32

*In-Situ PCR or Antibody Analysis (15 minutes)*

*Procedures for detecting variety of biomarkers and analytes including bacteria/virus, biomarkers, hmw DNA/RNA and antibody complexes*

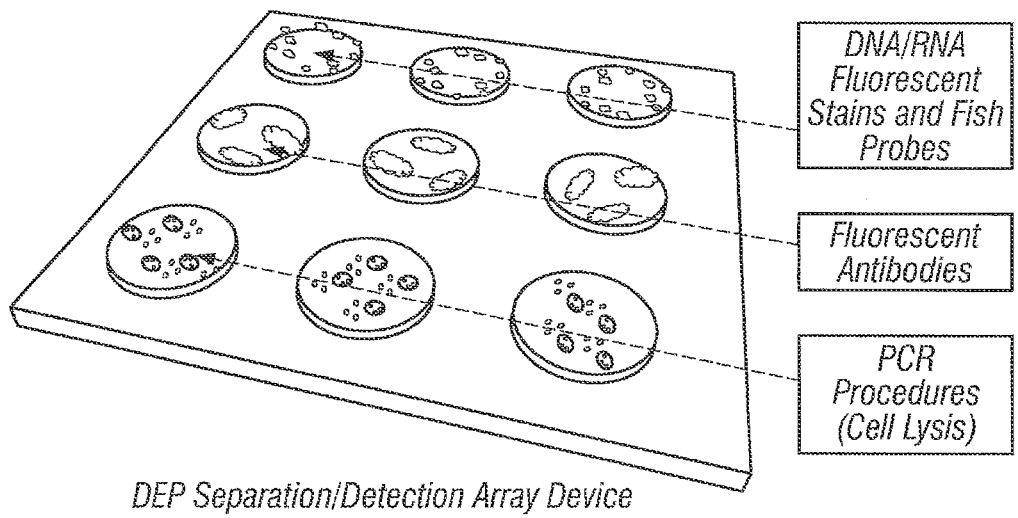

DNA/RNA Fluorescent Stains and Fish Probes

Fluorescent Antibodies

PCR Procedures (Cell Lysis)

DEP Separation/Detection Array Device

FIG. 33

*Post In-Situ Fluorescent Staining, Fluorescent Immunoassay, FISH and PCR Procedures for a Variety of Biomarkers and Analytes Including Cells, Bacteria/Virus, Cellular Nanoparticulates (CNP), hmw DNA/RNA and Antibody Complexes*

"Seamless Sample to Answer Diagnostics"

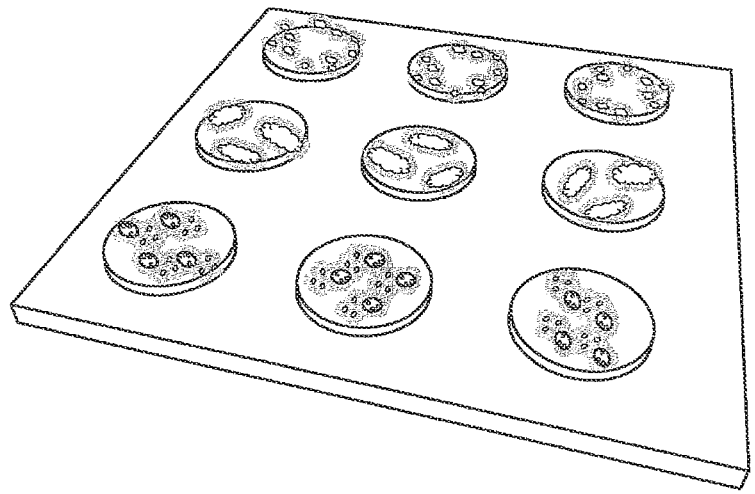

FIG. 34

EX-VIVO MULTI-DIMENSIONAL SYSTEM FOR THE SEPARATION AND ISOLATION OF CELLS, VESICLES, NANOPARTICLES, AND BIOMARKERS

CROSS-REFERENCES TO RELATED APPLICATIONS

This application is a Divisional Application of U.S. Ser. No. 12/936,147, filed Jan. 26, 2011, which is a National Stage application under 35 U.S.C. 3.71 that claims the benefit of PCT/US2009/039565, filed Apr. 3, 2009, which claims the benefit of U.S. Provisional Application No. 61/042,228 filed Apr. 3, 2008 entitled "Ex-Vivo Multi-Dimensional System for the Separation and Isolation of Cells, Vesicles, Nanoparticles and Biomarkers", the disclosures of which are incorporated herein by reference in their entirety.

STATEMENT AS TO RIGHTS TO INVENTIONS MADE UNDER FEDERALLY SPONSORED RESEARCH AND DEVELOPMENT

This work was supported by NIH Grant/Contract CA119335. The Government of the United States of America may have certain rights in this invention.

BACKGROUND

In biomolecular research and clinical diagnostics it is both important and a challenge to separate and identify rare cells, bacteria, virus, and biomarkers (e.g. DNA, RNA, antibodies, other proteins, etc.) in complex fluid samples like blood, plasma, serum, saliva, and urine. Additionally, the advent of bio-nanotechnology has led to numerous drug delivery approaches that involve encapsulation of drugs and imaging agents within nanovesicles and nanoparticles. Such approaches mean it will now also be important to identify and separate residual nanovesicles and nanoparticles that remain in the blood stream. A variety of physical, electronic, and biological techniques and mechanisms can be used for sample preparation and isolation of specific cells, nanovesicles, and biomolecules from complex samples like blood. These techniques and mechanisms include centrifugation, gel filtration, affinity binding, DC electrophoresis, and various combinations incorporated into lab-on-a-chip, microfluidic devices, and sample-to-answer systems.

Many of these conventional techniques (or combinations) are relatively time consuming processes that are not without problems and limitations. In particular, the isolation of rare cells (cancer cells, fetal cells, and stem cells), low numbers of bacteria and virus or very low numbers of specific antibodies, proteins, enzymes, DNA, and RNA molecules, still remains difficult. In the case of clinical diagnostics, rare cell and biomarker detection may also be limited by sample size; i.e., only a relatively small amount of blood may be drawn from very ill patients, the elderly and infants. Thus, sample preparation processes that are inefficient or require high dilution of the original sample often fail or are unreliable for isolating cells and other disease-related markers at lower concentration ranges. This is in particular a problem for early detection of cancer, residual disease, fetal cells/DNA/RNA in maternal blood, bacteria and virus in blood (septic infection), and the detection of low numbers of pathogens (e.g. bacteria, virus, etc.) and bioterror agents in large volumes of air, water, or in food stuffs.

Alternating current electrokinetic techniques that involve the use of AC fields to manipulate cells and nanoparticles offers some particularly attractive mechanisms for the separation of cells [see References 2-5], biomarkers (DNA [Ref. 5-8], proteins [Ref. 9], etc.), and ultimately drug delivery nanovesicles [Ref. 10]. These techniques can be broken down into three distinct phenomena: (1) AC electroosmosis, which is surface fluid flow due to the surface charge on an electrode; (2) electrothermal flow, which is bulk flow in solution due to thermal gradients produced by the electric fields; and (3) dielectrophoresis (DEP), which is an induced motion of particles produced by the dielectric differences between the particles and media in an AC electric field [Ref. 10]. Unfortunately, most conventional forms of DEP and related electrokinetic effects have problems that limit the usefulness of these technologies for clinically relevant sample preparation and diagnostics.

First, efficient DEP separations in terms of speed and control of selectivity usually have to be carried out at relatively low conductance on the order of <10-100 mS/m [Ref. 11]. Additionally, the ability to isolate the desired entities/analytes such as nanoparticles or DNA biomarkers in the positive or DEP high field regions (usually around or on the electrodes) becomes more difficult as the solution ionic strength increases and the conductance becomes greater than 10 mS/m. Thus, biological samples such as blood or plasma that have ionic strengths in the 100-200 mM range (conductance ~500-1000 mS/m) must be significantly diluted and/or processed before DEP separations can be carried out [Ref. 13, 14]. This alone often limits the usefulness of DEP for clinical diagnostics involving the detection of rare cells or low numbers of biomarkers. In cases where a sample (one ml blood) has to be diluted 100 to 1000-fold, now means that a very large sample volume must be processed, which can be prohibitively time consuming. If cells are first concentrated by physical mechanisms such as centrifugation or filtration and then are diluted into low conductance buffers, these processes are not only time consuming, but also costly and cause considerable perturbation to the sample. In the case where DEP might be used for stem cell separations, dilution into low ionic strength, less physiological-type buffers may result in perturbation of sensitive stem cells and may affect their further differentiation. The isolation of DNA, RNA, and protein biomarkers from blood is also important for future clinical diagnostics, in particular for monitoring cancer chemotherapy [Ref. 15], residual disease [Ref. 16], and early detection of cancer [Ref. 17].

While DEP has been used for the isolation of DNA and proteins, problems and limitations do exist in using DEP to carry out the detection of DNA in blood. The first problem again is the need to dilute and/or process the blood sample before DEP analysis. In the case of clinically relevant cell-free circulating DNA and RNA biomarkers in blood, finding and measuring the amount of DNA/RNA, its size and base composition (mutations and polymorphisms) is important [Ref. 17-19]. Sample processing that involves or requires centrifugation, filtration, and washing procedures can cause the release of DNA molecules by normal cells that are damaged or lysed in the process, as well as shear the clinically relevant DNA into smaller fragments. The release of extraneous DNA fragments and processing damage to the clinically relevant DNA greatly compromises and limits the diagnostic value of using such procedures. Such sample processing is also highly inefficient, and up to 60% of the DNA and over 90% of the RNA in the blood can be lost during the procedure [17].

A second problem area is that most DEP separation devices that have been used for DNA, protein, and nanoparticle separations use either polynomial gold microelectrodes created with a very small separation (6 µm or less) between them to serve as particle traps; or use castellated gold microelectrode arrays with 6-8 microns or less separation between them [Ref. 18-19]. These gold microelectrode array devices are usually fabricated by sputtering gold unto a glass substrate material. There are also a number of DEP approaches involving the use of nanoelectrodes [20]. The problem with these approaches are that the arrays have intrinsically low throughput, since the actual space to capture DNA or other biomolecules is relatively small and the electric field effect is significantly reduced when distance from the nanoelectrode increases (e.g. >10 nm). If this type of device is scaled for sample preparation (e.g., to process 1-10 ml of blood), the actual sample area that can be interrogated by the limited DEP field near the electrodes means that most of the DNA will be missed, or an extremely long sample processing time would be required. If the device is designed to constrict the liquid flow so as to pass within ten's of nanometers of the nanoelectrodes, then the processing time is again extremely long or a massively large (x-y dimension) device would be required. A variety of other problems exist including uncontrolled fluidic eddy currents due to other electrokinetic effects and osmotic forces. In other DEP applications, arrays that utilize circular platinum microelectrodes (50 µm to-80 µm diameter) with about 200 um spacing and over-coated with a porous hydrogel have also been used to carry out the DEP separation of bacteria from blood, and for the separation of cancer cells [Ref. 13, 14]. Again, for these DEP separations, the blood sample was centrifuged and a small fraction of the cells were re-suspended in a low ionic strength buffer [Ref. 13, 14, 24-26].

A third general problem for AC electrokinetic techniques is often that the resulting sensitivity versus specificity ratios are not sufficiently high for carrying out important or clinically relevant separations. For cell separations using dielectrophoresis (DEP), carrying out efficient rare cell separations with ratios of one in a million is difficult. Because many early disease diagnostics require rare cell or low level biomarker detection, it is important to be able to improve sensitivity versus specificity ratios as much as possible. In general, most DEP devices are not scaled properly to deal with the clinical reality of rare cell or low level biomarker isolation and detection, where a relatively large sample of from 1-10 ml of blood might be necessary for simple statistical reasons. When DEP device are designed for large samples, they are usually inefficient and unable to operate at high conductance conditions, and thus require further sample dilution.

A fourth problem for AC electrokinetic techniques is carrying out efficient (low loss) and highly selective separation processes in complex biological samples (e.g. blood, plasma, serum, etc.) for analytes and biomarkers which include; rare cells, bacteria, virus, DNA, RNA and proteins where all the entities might have 2-3 orders of magnitude difference in size range, and it is still necessary to achieve an efficient separation between entities that are more similar in size and composition. One important example is the separation of DNA nanoparticulates (20-50 kb), high molecular weight DNA (5-20 kb), intermediate molecular weight DNA (1-5 kb), and lower molecular weight DNA (0.1-1 kb).

The final and most serious problem for AC electrokinetic (DEP) devices and techniques is the introduction of electrochemistry that becomes more pronounced in higher conductance solutions (>100 mS/m), at lower AC frequencies (<20 kHz) and at higher voltages (>20 volts pt-pt). As will be shown in the Detailed Description section of this document, such electrochemistry can cause a number of adverse effects including bubbling, heating, fluidic turbulence, electrode degradation, and destruction of labile analytes. These adverse effects greatly limit the overall DEP device performance, prevent the accumulation, isolation, and detection of specific entities (cells, nanoparticles, DNA and proteins) from occurring in the DEP high field regions, and interfere with the isolation of cells and analytes into the DEP low field regions.

Other types of AC electrokinetic devices have been used to separate cells and nanoparticles, but have not proved viable in high conductance solutions. One of the most convincing arguments for the non-viability of AC electrokinetic and DEP devices is the fact that unlike DC electrophoresis, which has widespread use in biological research and clinical diagnostics, DEP has not been used for any practical applications. It would be desirable to perform dielectrophoresis with high performance characteristics that allow separations in high conductance biological samples and buffers.

SUMMARY

Embodiments of the present invention relate to novel sample preparation, sample-to-answer and point-of-care systems, devices, methods, and techniques that involve unique combinations of multidimensional AC electrokinetic and dielectrophoretic (DEP), DC electrophoretic, on-device microelectrophoresis and fluidic techniques for separating and identifying rare cells, bacteria, virus, drug delivery nanovesicles and nanoparticles, cellular organelles and structures (nuclei, mitochondria, vacuoles, chloroplasts, cylomicrons, etc.), cell-free circulating DNA/RNA biomarkers and other disease-related cellular nanoparticulates (e.g. partially degraded cellular components which are released into the blood, lymph or organs by cancerous, diseased or damaged cells), antibodies, antibody complexes, proteins, enzymes, and drugs and therapeutics directly in blood or other biological samples or buffers. In the disclosed embodiments, a combination of continuous and/or pulsed electrokinetic/dielectrophoretic (DEP) forces, continuous and/or pulsed field DC electrophoretic forces, on-device microelectrophoresis size separation, and controlled fluid flow (externally pumped and/or DC/AC electrokinetic driven) are utilized via novel chambered devices and other devices that incorporate arrays of robust electrodes (micro and/or macro sized) with over-layered porous structures which are used to carry out complex sample preparation, biomolecule separations, and diagnostic analyses.

This specification first discloses novel electrokinetic DEP devices and systems in which the electrodes are placed into separate chambers and positive DEP regions and negative DEP regions are created within an inner chamber by passage of the AC DEP field through pore or hole structures. Various geometries can be used to form the desired positive DEP (high field) regions and DEP negative (low field) regions for carrying cell, nanoparticle, and biomarker separations. Such pore or hole structures can contain (or be filled with) porous material (hydrogels) or can be covered with porous membrane type structures. By segregating the electrodes into separate chambers, such pore/hole structure DEP devices basically eliminate any electrochemistry effects, heating, or chaotic fluidic movement from occurring in the inner separation chamber during the DEP process (see FIG. 1 and FIG. 2).

The specification also discloses the use of scaled sectioned (x-y dimensional) arrays of robust electrodes and strategically placed (x-y-z dimensional) arrangements of auxiliary electrodes that combine DEP, electrophoretic, and fluidic forces so that clinically relevant volumes of blood, serum, plasma, or other samples may be more directly analyzed under higher ionic strength/conductance conditions. This specification discloses the overlaying of robust electrode structures (e.g. platinum, palladium, gold, etc.) with one or more porous layers of materials (natural or synthetic porous hydrogels, membranes, controlled nanopore materials, and thin dielectric layered materials) to reduce the effects of any electrochemistry (electrolysis) reactions, heating, and chaotic fluid movement that occur on or near the electrodes, and still allow the effective separation of cells, bacteria, virus, nanoparticles, DNA, and other biomolecules to be carried out (FIGS. 3-8). In addition to using AC frequency cross-over points to achieve higher resolution separations, on-device (on-array) DC microelectrophoresis can also be used for the secondary separations. For example, the separation of DNA nanoparticulates (20-50 kb), high molecular weight DNA (5-20 kb), intermediate molecular weight DNA (1-5 kb), and lower molecular weight DNA (0.1-1 kb) fragments (FIGS. 9-12). The fact that the device can be sub-sectioned means concurrent separations of different blood cells, bacteria and virus, and DNA can be carried out simultaneously on such a device (FIGS. 13-16).

Embodiments of the present invention also relate to the use of temperature control to provide more selective and efficient cell separations (e.g. of cancer and stem cells). Embodiments of the invention thus relate in one aspect to ex-vivo sample preparation, seamless sample-to-answer, lab-on-a chip and point of care (POC) diagnostic systems that can be used to monitor and/or analyze blood for cancer cells, bacteria, virus, nanovesicles (drug delivery), nanoparticles, high molecular weight DNA nanoparticulates, cellular organelles, proteins, antibodies and antibody complexes, and a variety of other clinically relevant biomarkers of disease and metabolic state. Such ex-vivo systems and devices can monitor or scan the blood by AC electric fields, separating, isolating, highly concentrating, and detecting and analytes and clinically relevant entities. Systems can be used to selectively collect such entities for more complex analysis including but not limited to immunochemistry; DNA/RNA probe hybridization; polymerase chain reaction (PCR), rolling circle amplification (RCA), strand displacement amplification (SDA) and other techniques for genotyping, sequence analysis, gene expression all within the same sample chamber (seamless sample to answer), or via associated analytical devices and/or collection systems. A novel device constructed in accordance with the invention could be a point-of-care (POC) seamless sample-to-answer system that allows rapid molecular diagnostics to be rapidly carried out on an undiluted blood sample. Another novel device in accordance with the invention could be an ex-vivo cancer chemotherapy monitoring system that would allow blood to be shunted from the patient, rapidly analyzed (measure biomarker DNA, drug or drug delivery nanovesicle levels and isolate cancer cells), and then returned to the patient (via closed loop) with minimal dilution or physical/chemical perturbation to the sample. Such ex-vivo systems could also be used for monitoring other therapeutics, diseases, and patient dispositions, particularly in critical care situations.

The disclosed systems, devices, methods, and techniques embodying the invention allow the separation of cells, nanoparticles, and biomarker entities to now be carried out under higher conductance (>100 mS/m) ionic strength conditions, at lower AC (DEP) frequencies (<20 kHz), and at higher field strengths (>20 voltages pk-pk) than those used for most previous DEP separations. More specifically, DEP separations can be carried out not only under higher ionic strength conditions, but also directly in complex biological samples including blood, plasma, serum, and undiluted buffers where now nanoscale (500 nm to 5 nm) analytes and entities can be isolated in the DEP high field regions, while the larger entities (cells, micron particles, etc.) can isolated in the DEP low-field regions between the electrodes.

The new devices ameliorate the electrochemistry, heating, and chaotic fluidic effects that occur with the use of castellated DEP electrode arrays, which are currently a preferred method to separate nanoparticles and biomolecules. In another aspect, devices and processes can use more macroscopically scaled arrangements of robust multiple electrodes in sectioned arrays, which not only allows larger sample volumes to be more rapidly and efficiently interrogated, but essentially allows a very small number of cancer cells, bacteria, virus, nanoparticles, and nanoparticulates and very low concentrations of DNA, RNA biomarkers, and antibody complexes to be isolated from complex samples containing very large numbers of normal cells, i.e. blood. Essentially, the use of a "properly scaled" macroscopic system of electrodes changes the processes of finding one specific cell (or other entity) in a million, to finding one specific cell in one thousand, i.e., the sample is spread out over many subgroups of electrodes, creating a parallel hierarchical sorting mechanism. This separation process can be applied to treat blood, and will remove smaller-size DNA, RNA, and higher molecular weight DNA from proteins as well as cells. As a result of the size of the electrodes (10-100 micron diameter, with 20-100 micron separation) and ability to use less diluted samples, the separation process can now be completed in a rapid and high-throughput manner on scaled array devices, which have from 2-100 array sections, each section of which might contain from 100-1000 individual electrodes. The device would also incorporate strategically placed auxiliary electrodes in the x-y-z dimensions.

Embodiments described herein show that the disclosed array devices and systems can be used to separate out nanoparticles and cellular nanoparticulates in lower frequency ranges (10-50 kHz) from entities of larger sizes (cells and micron-size particles) based off of the Clausius Mossotti factor effects (along with other AC Electrokinetic phenomena) inherent in every nanoparticulate less than or equal to about 500 nm in diameter. This specification also discloses that when AC electrokinetics effects are used in conjunction fluid flow, the process will relieve excess heat build-up. This specification further discloses that when fluid flow and DC electrophoresis are combined with AC electrokinetics effects, both cells and proteins can be effectively moved downstream to the lower array section of the illustrated devices, while the highly negatively charged DNA nanoparticulates and DNA molecules can be concentrated upstream in the upper array section of the devices. Thus, the different array sections of the illustrated devices can now be used to carry a more selective separation process such as: multiplexing with red blood cell, white blood cell, cancer cell separations, and protein removal on the lower array section; bacteria, virus, nanoparticles and nanovesicles in the middle array section; and DNA nanoparticulates and DNA molecules on the upper array section of the devices.

Finally, this specification also discloses devices with separate electrode chambers and pore/hole structures leading to an isolated separation chamber, as well as robust electrode array devices that are over-layered with nanoporous materials (from one nanometer to one millimeter in thickness) that can be used to carry out simultaneous or subsequent secondary size-separation processes. For example, if the upper array section of an illustrated device can be used to concentrate a complex mixture of DNA components, then a combination of AC electrokinetics effects and DC electrophoretic forces can be used to achieve the secondary separation of DNA nanoparticulates from high molecular weight DNA (5-50 kb), intermediate molecular weight DNA (1-5 kb), and lower molecular weight DNA (0.1-1 kb). In addition, the illustrated embodiments permit DC microelectrophoresis within the nanoporous layers to be used to carry out the size separation of the various DNA fragments.

BRIEF DESCRIPTION OF THE DRAWINGS

FIG. 1 shows a new electrokinetic DEP device in which electrodes have been placed into separate chambers and DEP fields are created within an inner chamber by passage through pore structures.

FIG. 2 shows surface pore/hole geometry for new electrokinetic DEP device shown in FIG. 1.

FIG. 26A-C shows fluorescent and SEM images of 60 nm nanoparticles and electrode damage following high conductance DEP.

FIG. 31 shows a seamless sample-to-answer hmw-DNA process in blood comprising step 5.

FIG. 32 shows a seamless sample-to-answer process with complex sample.

FIG. 33 shows a seamless sample-to-answer complex sample process with PCR and immunoassay analyses.

FIG. 34 shows a seamless sample-to-answer complex sample process with PCR and immunoassay analyses and detection.

DETAILED DESCRIPTION

This document teaches novel sample separation and sample-to-answer systems, devices, methods, and techniques that combine multi-dimensional AC electrokinetics, including dielectrophoresis (DEP), DC electrophoretics, microelectrophoresis, and fluidics in unique ways that can be used to separate and identify cells, nanovesicles and nanoparticulates, bacteria and/or viruses, as well as a host of other clinically relevant biomarkers of disease from relevant volumes of high conductance (ionic strength) biological and clinical samples and buffers including but not limited to blood, plasma, serum, urine, lymph fluid, saliva, biopsied samples, cell cultures (stem cells), bacterial, and fermentation cultures. While disclosed embodiments of the invention enable the DEP separation of cells, nanoparticles, and other analytes to be carried out directly in undiluted samples (blood, plasma, biological buffers), the embodiments do not preclude the use of the disclosed devices and methods for partially diluted samples or buffers, or for samples that have gone through other sample preparation procedures.

Using novel multi-chambered devices and electrode array devices with robust electrodes of defined diameter and separation distances allows viable DEP to be carried out in high conductance (ionic strength) solutions. These novel DEP devices are designed in such a manner that bubbling, heating, and other adverse effects due to the increased electrochemistry that occurs under high conductance conditions does not reduce the efficiency or prevent the separation, concentration, and detection of specific analytes or entities from complex biological samples and high ionic strength buffers. Carrying out DEP separations under high conductance conditions has been a major problem and limitation for most problematic AC electrokinetic and dielectrophoretic separation devices [Ref. 1-28]. Even when some degree of high conductance DEP separations could be achieved for a short period of time using microarray devices with hydrogel over-coating the electrodes, such devices were not viable as a sample separation tool and diagnostic device [Ref. 13, 14, 24-28].

Figure 17A:
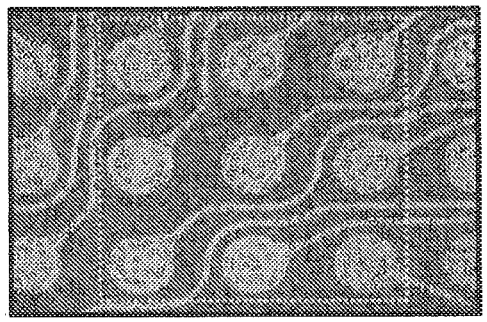
FIG. 17A-H shows DEP separation of 60 nm and 200 nm nanoparticles under intermediate and high conductance conditions.
Figure 17B:
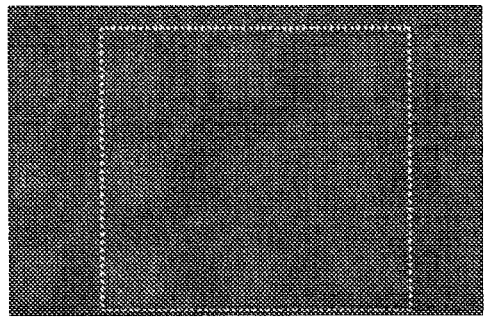
Figure 17C:
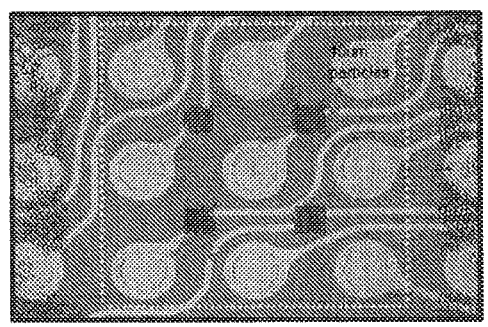
Figure 17D:
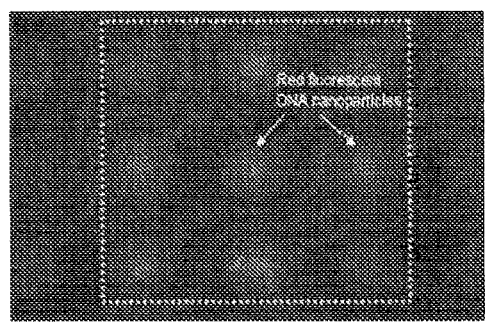
Figure 17E:
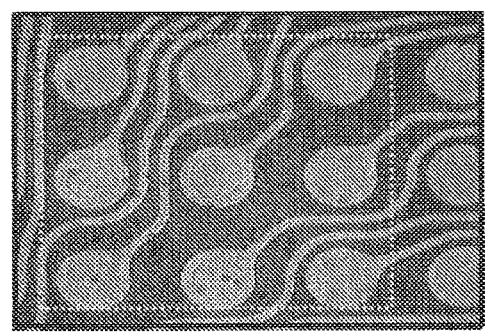
Figure 17F:
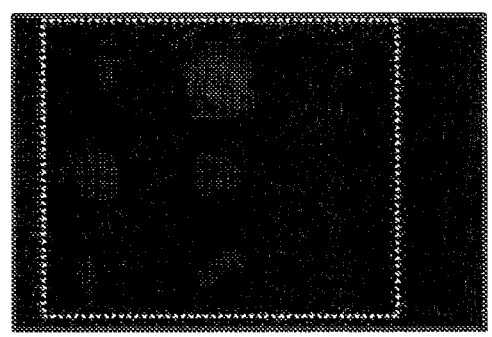
Figure 17G:
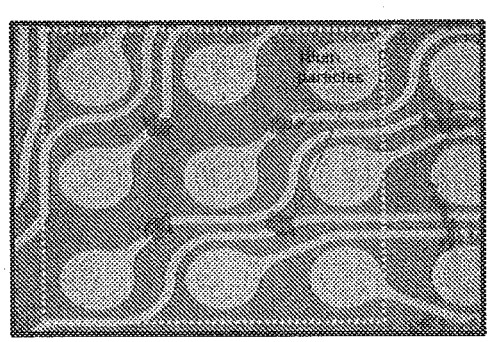
Figure 17H:
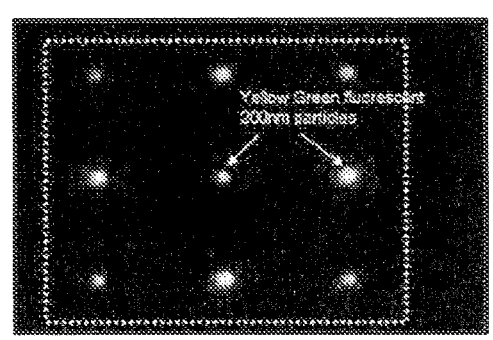

In order to better demonstrate this DEP conductance limitation, an initial first example described herein shows the DEP separation of nanoparticles in a low conductivity buffer. This example involves separating 60 nm DNA derivatized nanoparticles from 10 µm particles in MilliQ water (5.5 µS/m). The separation was carried out at 10 kHz AC at 10 volts peak to peak (pk-pk). FIG. 17a shows the initial conditions under white light before the AC electric field is applied with a random distribution of the 10 µm particles over the microelectrode array. The initial conditions under red fluorescence detection show a red fluorescent haze across the microarray as would be expected from the 60 nm DNA derivatized fluorescent nanoparticles (see FIG. 17b). After the AC DEP field was applied for only 30 seconds, most of the 10 µm particles have concentrated in very orderly arrangements into the negative DEP low field regions (see FIG. 17c). After a 1-minute application of the AC field, the 60 nm DNA derivatized nanoparticles have concentrated onto the positive DEP high field regions over the microelectrodes (see FIG. 17d). The high fluorescent intensity on the microelectrodes together with the decrease of fluorescent intensity in the surrounding areas indicates that most of the nanoparticles have concentrated into the high field regions. The next example shows the DEP separation of 200 nm nanoparticles mixed with 10 µm particles in 0.01×TBE (1.81 mS/m) carried out at 3 kHz AC at 10 volts pk-pk. The initial white light view shows a random distribution of the 10 µm particles before the field is applied (FIG. 17e), and the green fluorescence view shows no accumulation of the 200 nm nanoparticles in the high field regions (FIG. 17f). In less than 10 minutes, the 10 µm particles are concentrated into the low field regions (FIG. 17g), and the 200 nm nanoparticles are highly concentrated into the positive DEP high field regions (FIG. 17h). These low conductivity DEP results are generally consistent with other low conductivity DEP nanoparticle separations cited in the literature, and expected from classical DEP theory [Ref. 11-14].

Figure 18A:
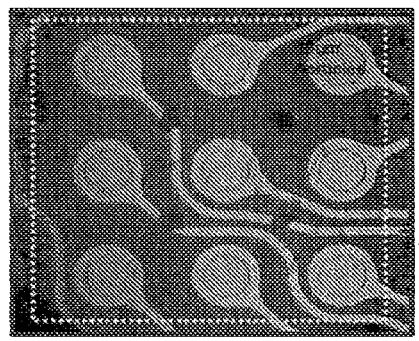
FIG. 18A-D shows DEP separation of 200 nm nanoparticles under intermediate and high conductance conditions.
Figure 18B:
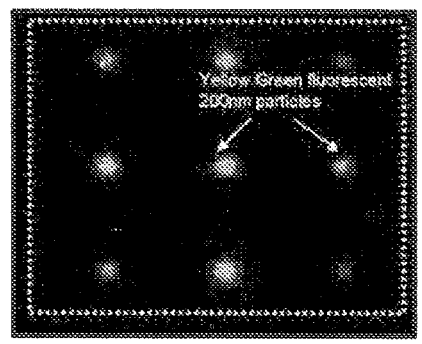
Figure 18C:
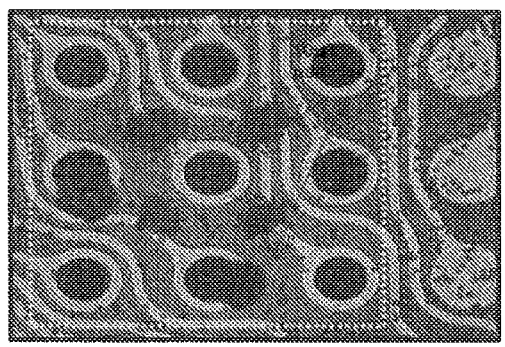
Figure 18D:
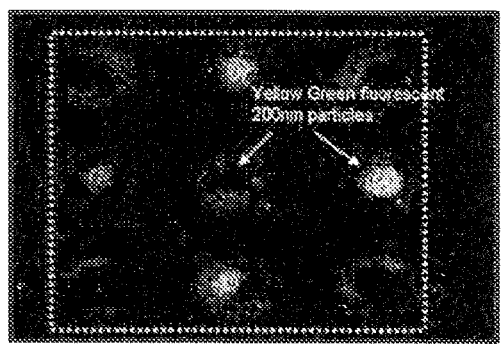

The next set of DEP examples shows the separations of 60 nm DNA derivatized nanoparticles, 200 nm nanoparticles, and 10 µm particles in buffer solutions with conductivities greater than 100 mS/m. For 1×TBE (0.109 S/m), after the AC field was applied for 20 minutes, the separation between 200 nm nanoparticles and 10 µm particles in under white light conditions showed the 10 µm particles concentrated in the low field regions (FIG. 18a). Under green fluorescence, the 200 nm nanoparticles were concentrated in the positive DEP high field regions on top of the microelectrodes (FIG. 18b). For DEP experiments carried out in 1×PBS (1.68 S/m), after 20 minutes the 10 µm particles are concentrated into the low field regions (FIG. 18c). The green fluorescence 20 minute image for the high conductance 1×PBS buffer experiment was taken after removal of some small bubbles and at an increased gain (FIG. 18d). The image shows that the 200 nm nanoparticles have concentrated into the positive DEP high field regions of four microelectrodes. The microelectrodes, however, now show significant darkening and two of the microelectrodes had bubbled. The observation that the 200 nm nanoparticles have predominantly concentrated on these four microelectrodes is consistent with the fact that they produce slightly higher fields.

Figure 19A:
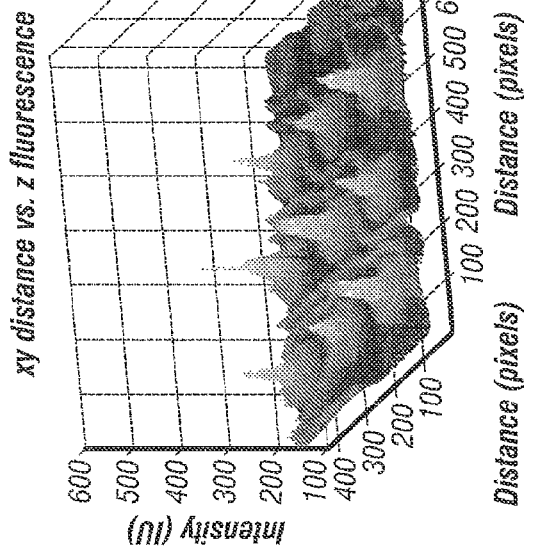
FIG. 19A-H shows 3D fluorescent intensity images for the DEP separation of 60 nm and 200 nm nanoparticles under intermediate and high conductance conditions.
Figure 19B:
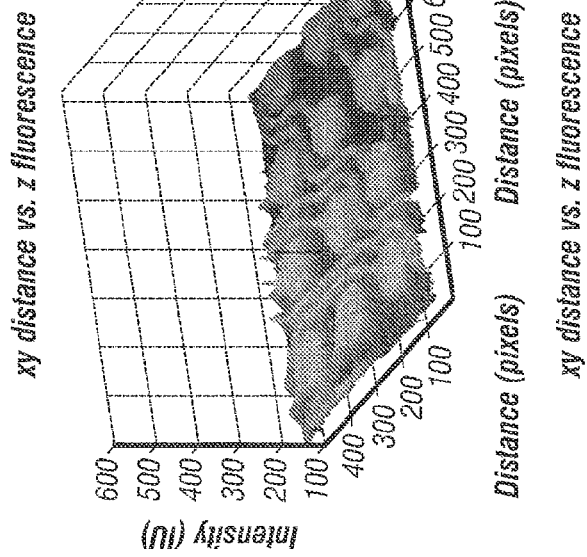
Figure 19C:
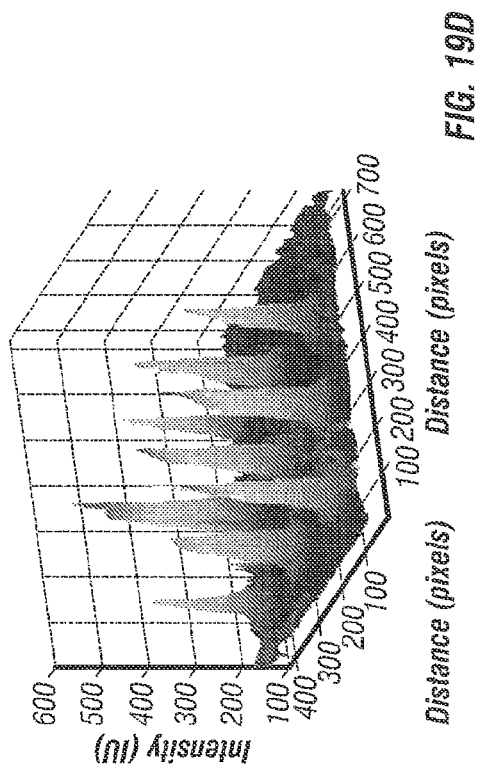
Figure 19D:
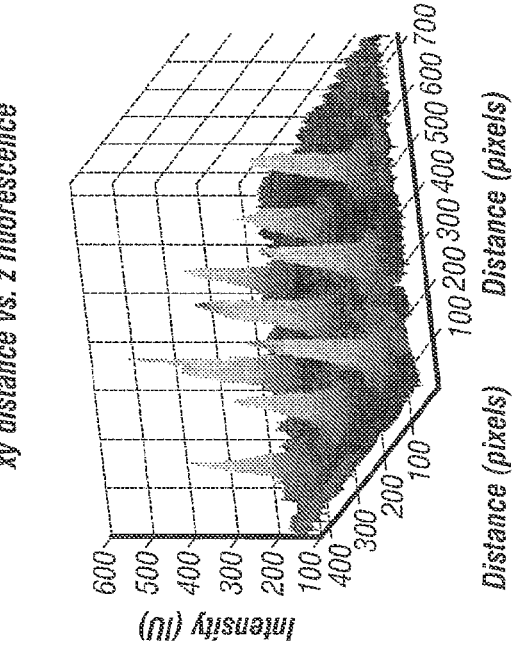
Figure 19E:
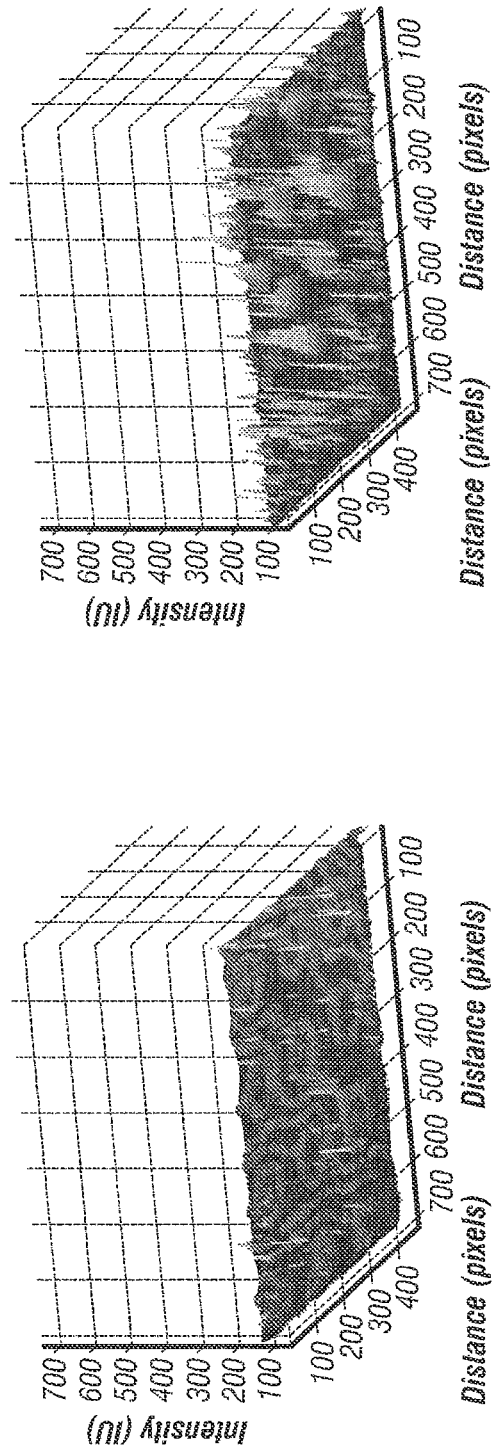
Figure 19F:
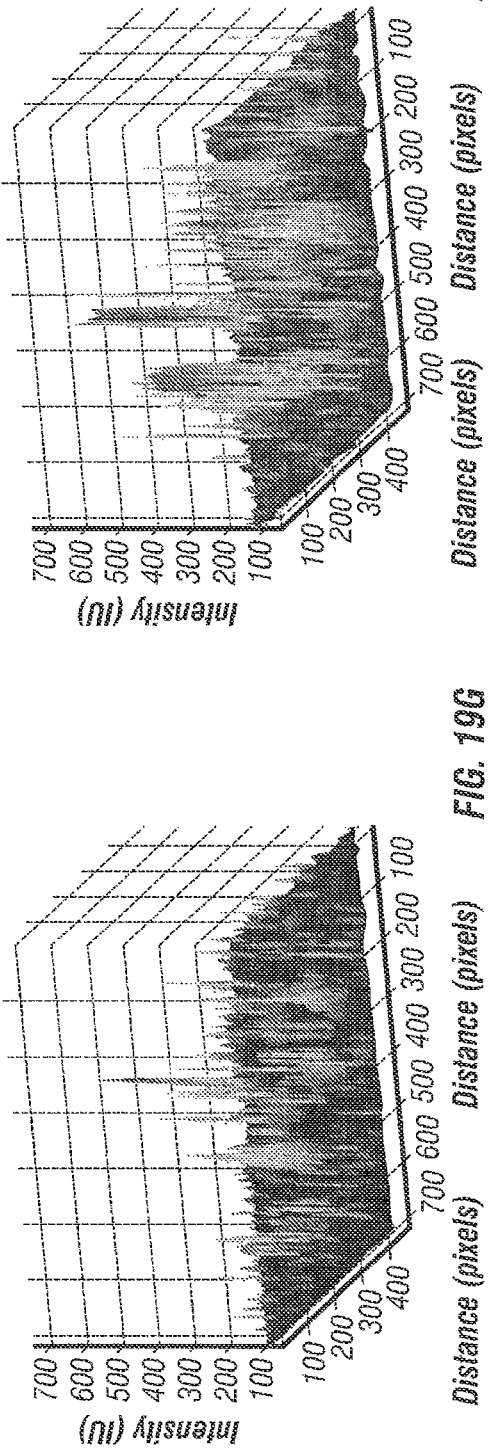
Figure 19G:
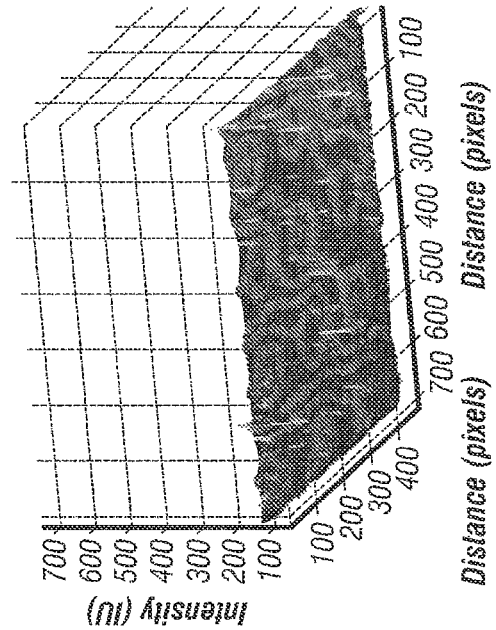
Figure 19H:
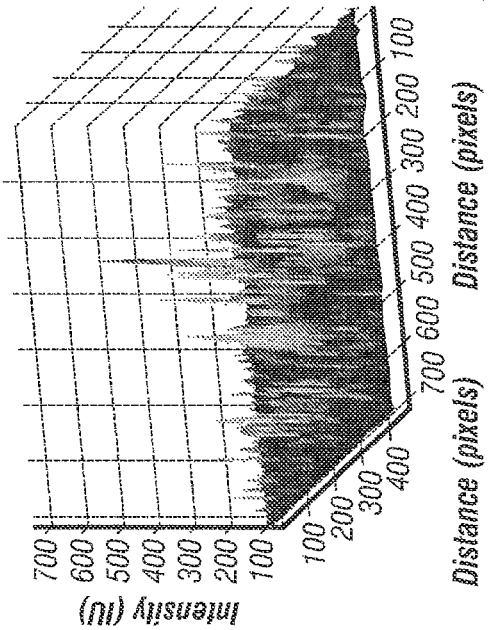

The high conductance experiments in 1×PBS buffer that were carried out using 60 nm DNA derivatized nanoparticles also yielded similar results, i.e., in that the 60 nm nanoparticles were still observed to concentrate in the positive DEP high field regions over three of the microelectrodes. Further analysis of the fluorescence images was performed in a mathematical model using MATLAB to produce three-dimensional peaks, which better demonstrate the concentration of the fluorescent nanoparticles over the high field regions. For the 1×TBE experiments with 60 nm DNA derivatized nanoparticles, the 3D fluorescent data showed a significant increase from time points 0 minutes (FIG. 19a), 2 minutes (FIG. 19b), 8 minutes (FIG. 19c), and 16 minutes (FIG. 19d). Similarly, the 3D fluorescent data for the 200 nm nanoparticles in 1×PBS also shows an increase from time points at 0 minutes (FIG. 19e), 8 minutes (FIG. 19f), 16 minutes (FIG. 19g), and after 20 minutes (FIG. 19h).

Figure 20A:
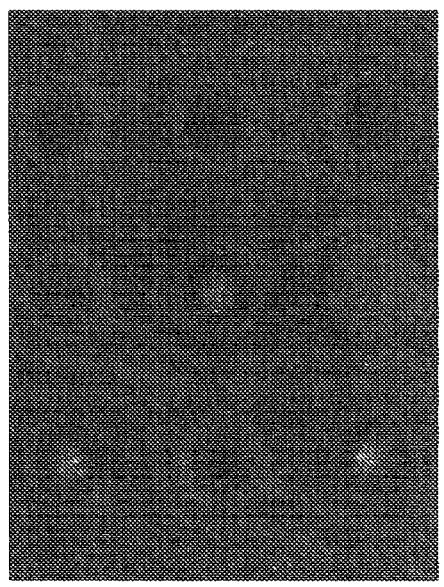
FIG. 20A-D shows real image and 3D intensity images for the DEP separation of 60 nm nanoparticles high conductance conditions.
Figure 20B:
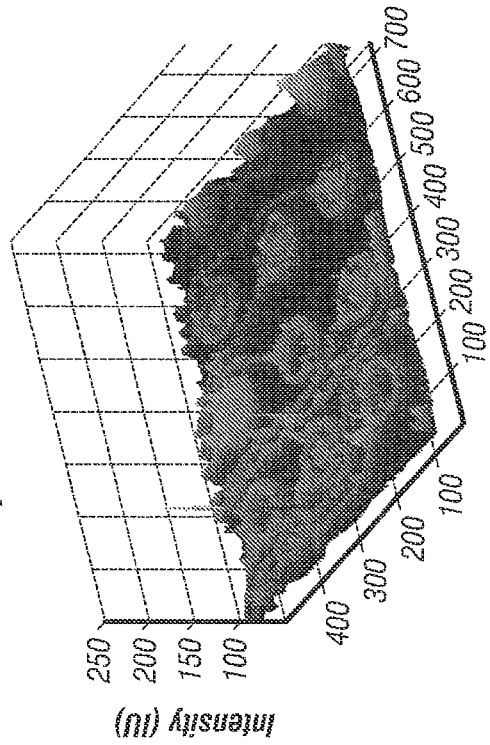
Figure 20C:
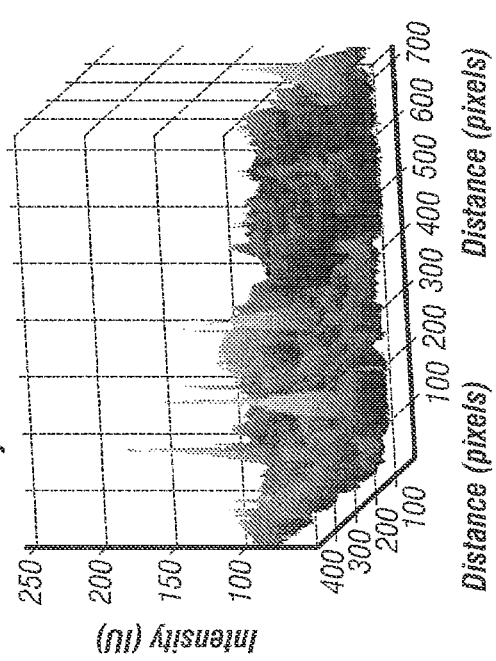
Figure 20D:
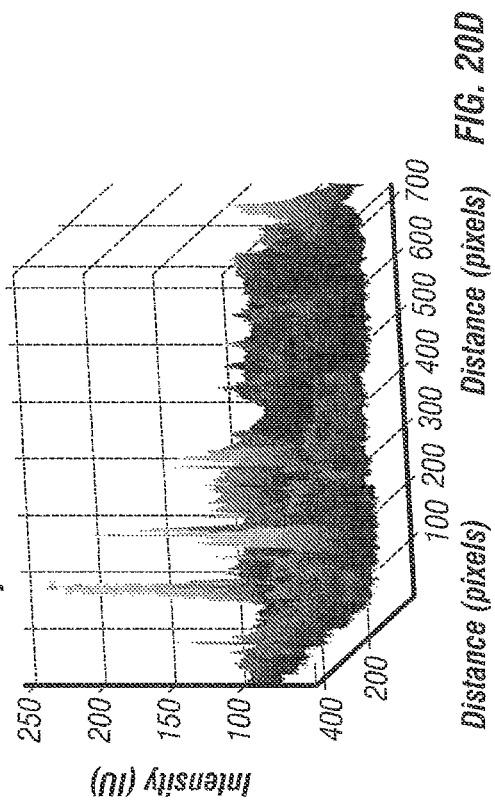
Figure 21A:
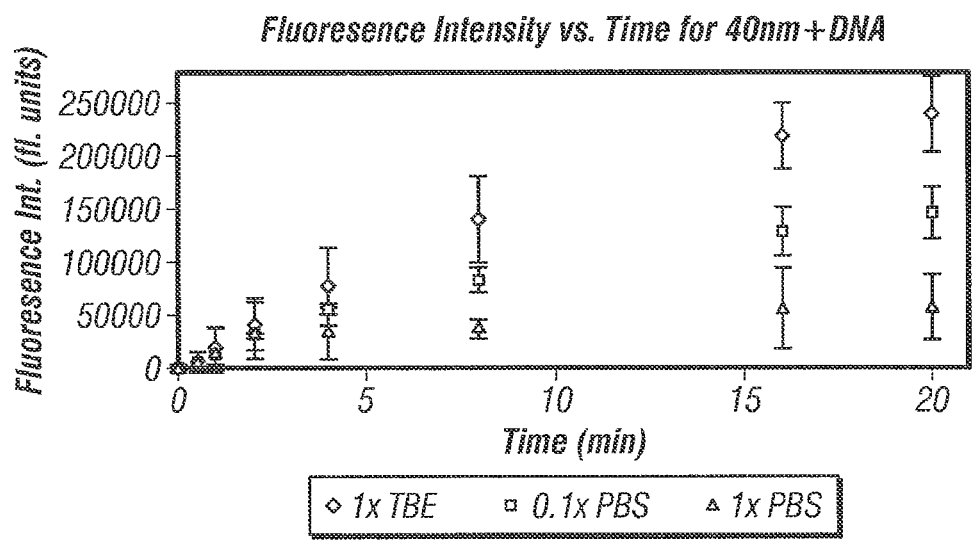
FIG. 21A-B shows graphs of nanoparticle fluorescent intensity increase versus increasing conductance for 60 nm and 200 nm nanoparticles.
Figure 21B:
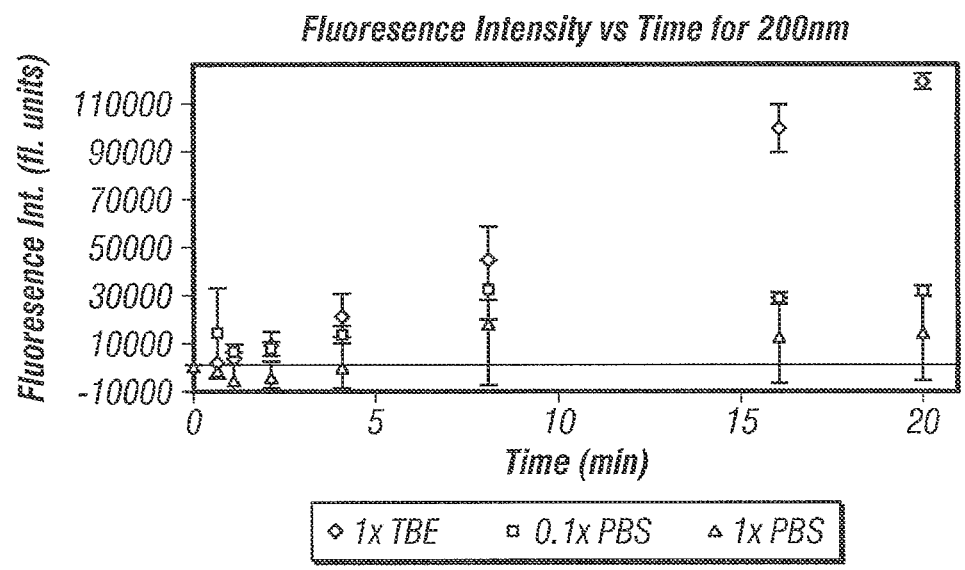

For the 60 nm DNA derivatized nanoparticles in 1×PBS, there is still concentration as is seen in as seen in the fluorescent image (FIG. 20a). The 3D fluorescent image data also shows a similar fluorescence increase from 0 minutes (FIG. 20b), to 8 minutes (FIG. 20c) and to 20 minutes (FIG. 20d). Due to the inactivation of one of the microelectrodes (third row, second column) shown in FIG. 20a, the electric field pattern is slightly altered. The overall fluorescence data was compiled using MATLAB for experiments in buffers of 1×TBE, 0.1×PBS (0.177 S/m) and 1×PBS at the time points of 0, 0.5, 1, 2, 4, 8, 16, and 20 minutes. The results for the 60 nm DNA derivatized nanoparticles are shown in graph (FIG. 21a), and the results for the 200 nm nanoparticles are shown in graph (FIG. 21 b). These examples show an increase in concentration of the fluorescent nanoparticles over time. More importantly, these examples also show a significant decrease in overall concentration of the fluorescent nanoparticles as the conductivity of the buffers increases, i.e., a much longer time is needed to concentrate entities at the higher conductance conditions.

Figure 22:
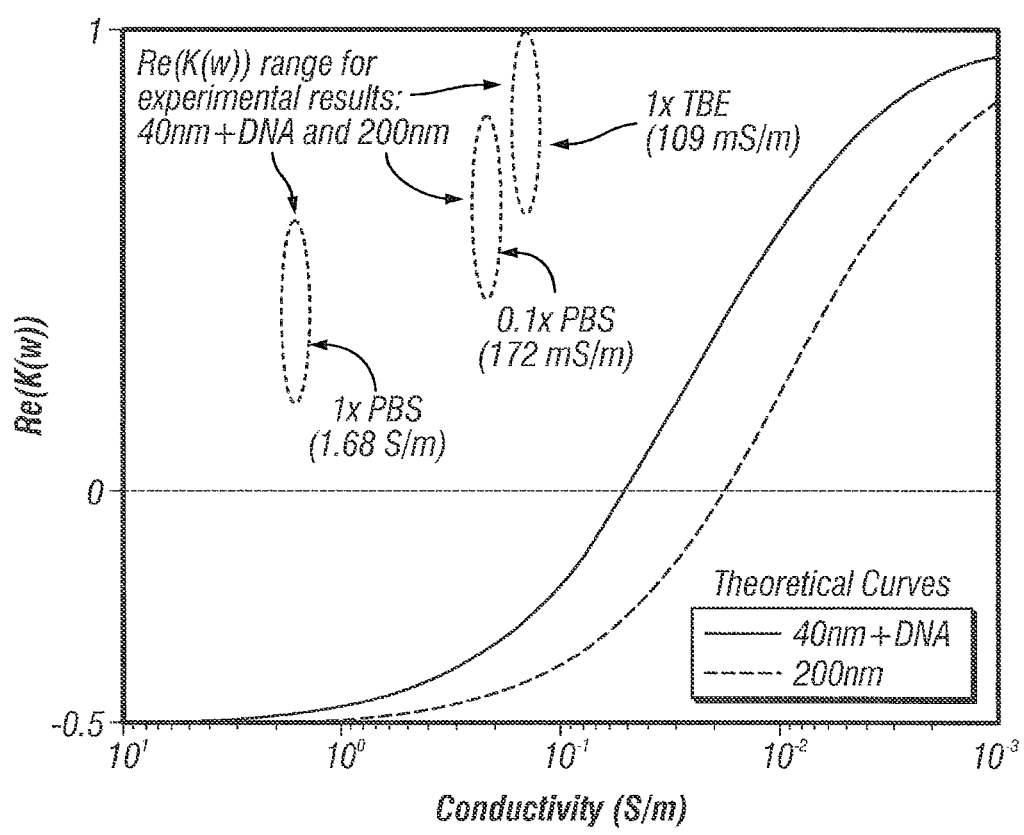
FIG. 22 shows graph of the experimental results versus theoretical DEP crossover curves for 60 nm and 200 nm nanoparticles as function of conductance.

FIG. 22 now shows the theoretical curves and the ranges for the experimental results for the real part of the Clausius-Mossotti factor ($Re(K(\omega))$) versus conductivity for the 60 nm DNA derivatized nanoparticles and the 200 nm nanoparticles. The graph indicates that the theoretical $Re(K(\omega))$ values should be negative for the conductivities used in these examples, and therefore the nanoparticles should have accumulated in the low field regions. Nevertheless, the actual results show that accumulation of nanoparticles continues in the high field region. Unfortunately, under these high conductance conditions, (>100 mS/M) bubbles, electrode darkening, and electrode failures occur, and much longer DEP times are required which produce relatively inefficient separations.

Figure 23B:
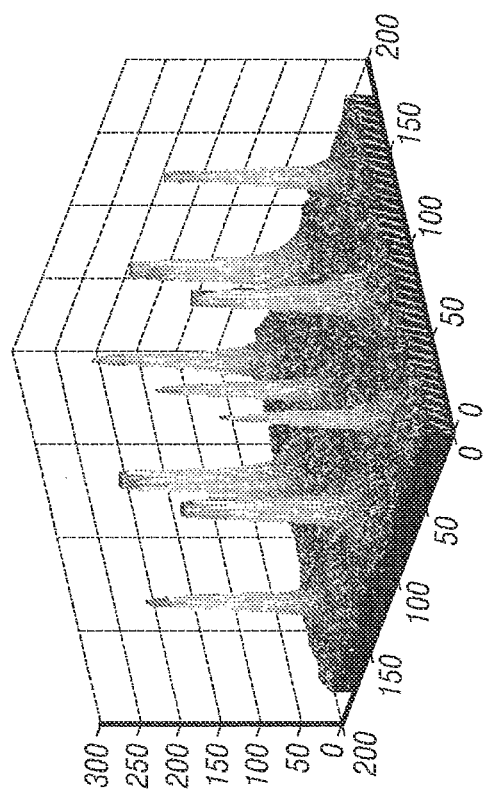
FIG. 23A-H shows both real images and 3D intensity images for the DEP separation of 200 nm nanoparticles on un-coated and hydrogel over-coated platinum electrodes at increasing conductances (shows electrode darkening).
Figure 23D:
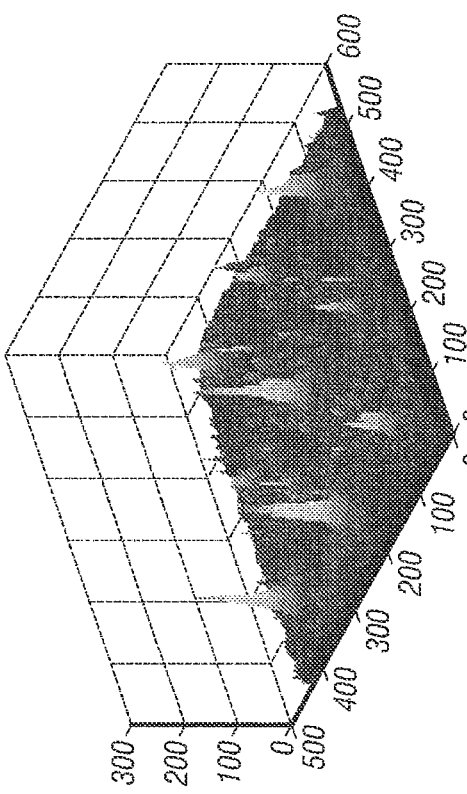
Figure 23A:
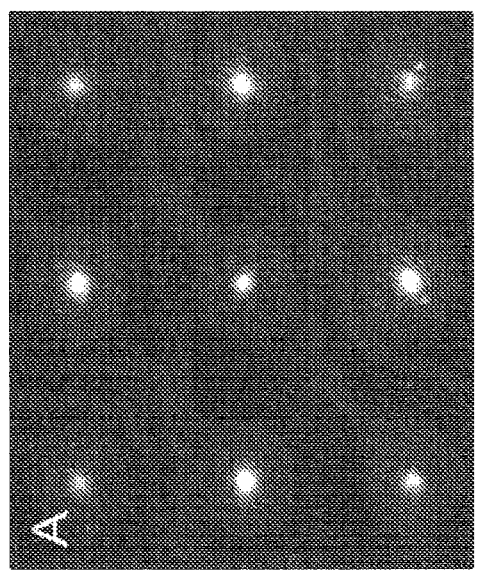
Figure 23C:
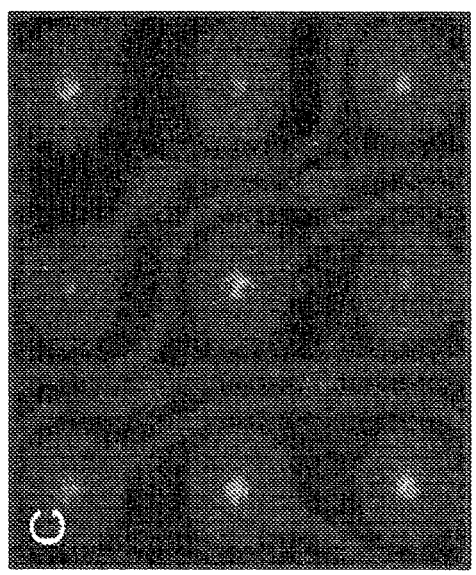
Figure 23E:
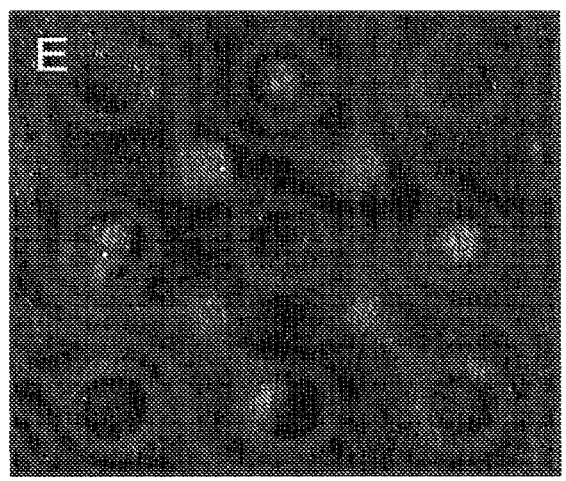
Figure 23F:
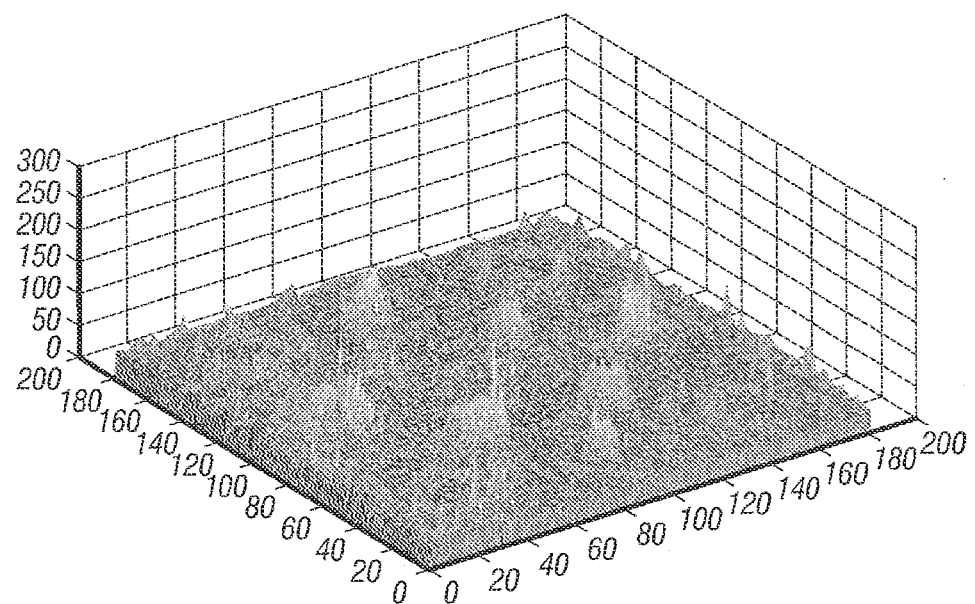
Figure 23G:
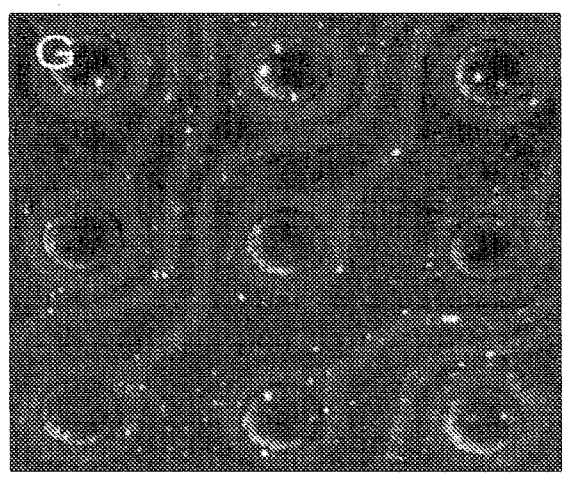
Figure 23H:
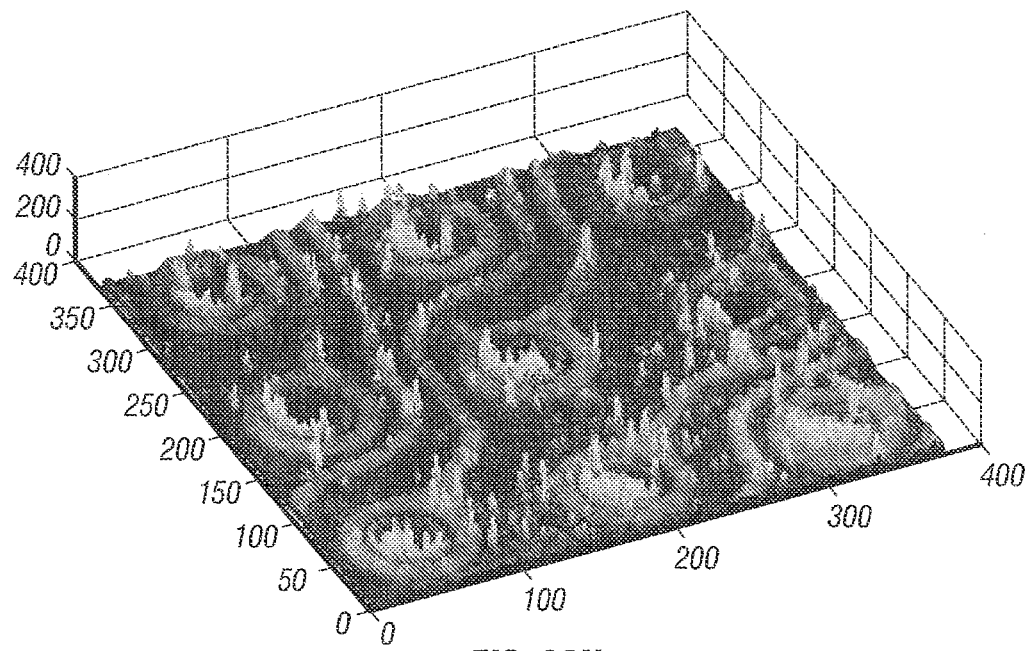

It has been discovered that these DEP-related adverse effects are due to the increased electrochemical activity that occurs when using higher ionic strength buffers that contained sodium ($Na^+$) and chloride ($Cl^-$) electrolytes [Ref. 29-30]. A better understanding of these effects was necessary to develop more viable and robust DEP devices for molecular diagnostic applications. Further examples that clearly demonstrate the microelectrode/nanoparticle/electrolyte adverse interactions under high conductance conditions are now shown in the examples described herein. These examples involved carrying out the separation and detection of 200 nm yellow-green fluorescent polystyrene nanoparticles from 10 micron spheres under different conductance (ionic strength) conditions, on platinum microelectrode structures with hydrogels (FIG. 23 A-F), and without a hydrogel layers (FIG. 23 G-H). The results for all buffers (0.01×TBE, 1×TBE, 1×PBS) show the separation and concentration of the green fluorescent 200 nm nanoparticles into the DEP high field regions over the microelectrodes, and the concentration of the 10 μm spheres into the low field regions between the microelectrodes. Again, the concentration of 200 nm nanoparticles appears highest for 0.01×TBE, and decreases as the buffer ionic strength increase to 1×PBS (see FIGS. 23B, 23D, 23F, and 23H). The concentration of nanoparticles occurs more at the center of microelectrodes with hydrogels, and at the outside perimeter for the uncoated microelectrodes (FIG. 23A, 23C, 23E, 23G). At the highest buffer conductance (1×PBS), both the hydrogel over-coated microelectrodes (FIG. 23E) and the uncoated microelectrodes show significant darkening of the electrodes (FIG. 23G).

While not shown in these drawing figures, increased micro-bubbling was also observed in 1×PBS buffer on both the hydrogel over-coated and the uncoated microelectrodes after four minutes of DEP. Nevertheless, the micro-bubbling appeared more pronounced on the uncoated microelectrodes. Also, in a 1×PBS buffer, chaotic bubbling occurs over almost all the electrodes when the AC voltage is increased above 20 volts pt-pt. While nanoparticle concentration and darkening could be observed on both the hydrogel overcoated and the uncoated platinum microelectrodes, the uncoated microelectrodes provided an opportunity to use scanning electron microscopy (SEM) to analyze the electrochemical effects and to verify nanoparticle concentration and adhesion.

Figure 24A:
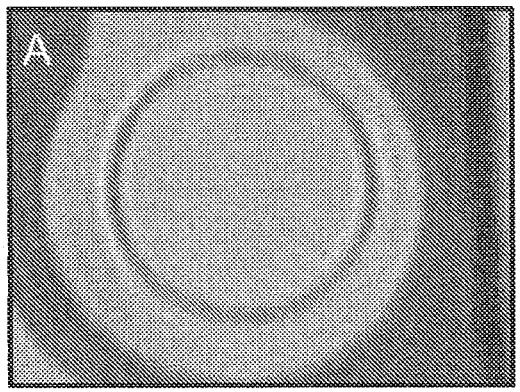
FIG. 24A-F shows light microscope and SEM images of electrode damage following high conductance DEP without nanoparticles present.
Figure 24B:
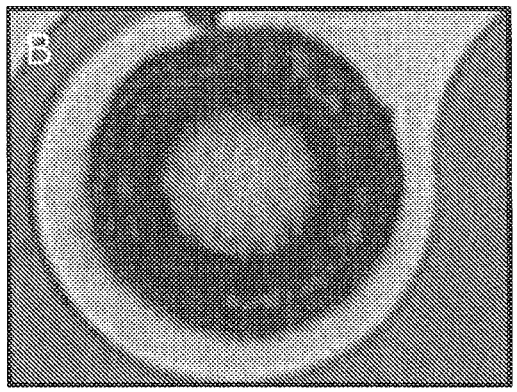
Figure 24C:
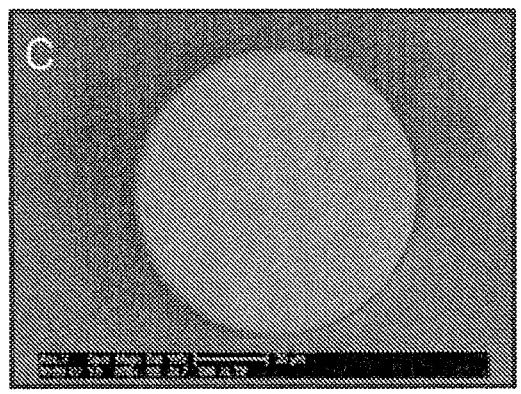
Figure 24D:
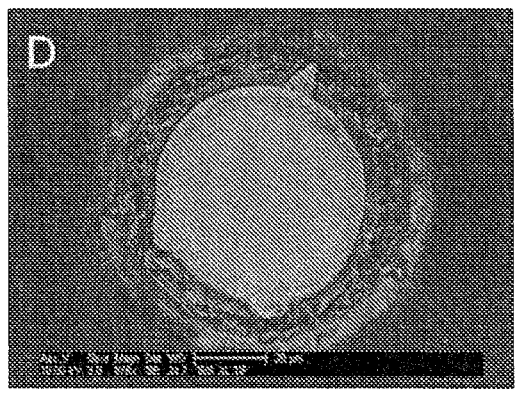
Figure 24E:
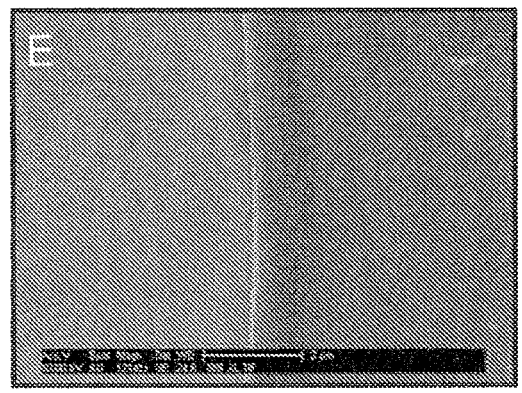
Figure 24F:
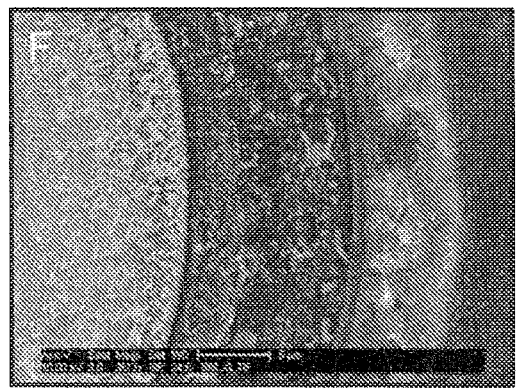

In the next set of examples, DEP was carried out in high conductivity 1×PBS buffer on uncoated microelectrodes with no nanoparticles present. The microelectrode array was washed, dried, and then imaged using SEM. FIG. 24A first shows the light microscope images of an un-activated control microelectrode, and an activated microelectrode (FIG. 24 B) after 10 minutes of DEP at 3000 Hz, 10 volts pk-pk. Significant darkening of the activated microelectrode is clearly observed. FIGS. 24C and 24D now show the SEM images of the same un-activated and activated microelectrodes. Significant damage and degradation of the activated microelectrode is clearly observed in the SEM image. FIGS. 24E and 24F are higher magnification SEM images of the microelectrodes, and show even more clearly the degradation of the platinum layer that has occurred around the microelectrode perimeter (FIG. 24F).

Figure 25A:
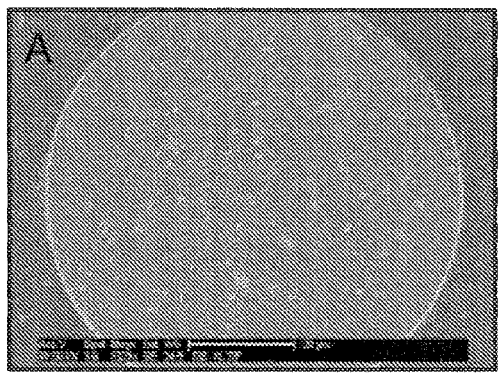
FIG. 25A-H shows SEM images of electrode damage and fusion of 200 nm nanoparticles following high conductance DEP.
Figure 25B:
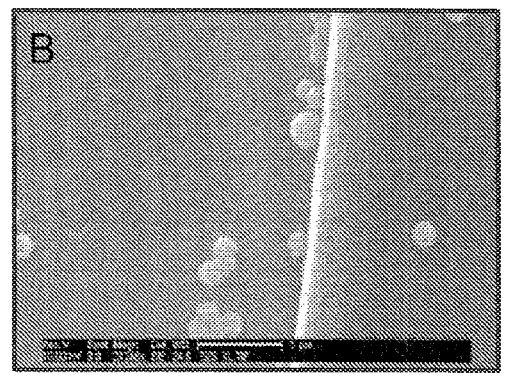
Figure 25C:
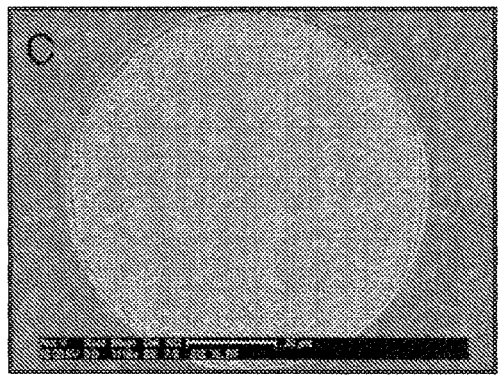
Figure 25D:
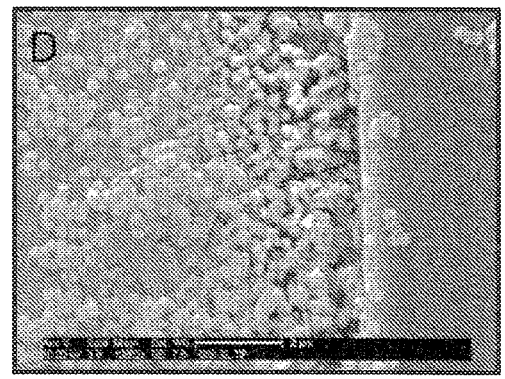
Figure 25E:
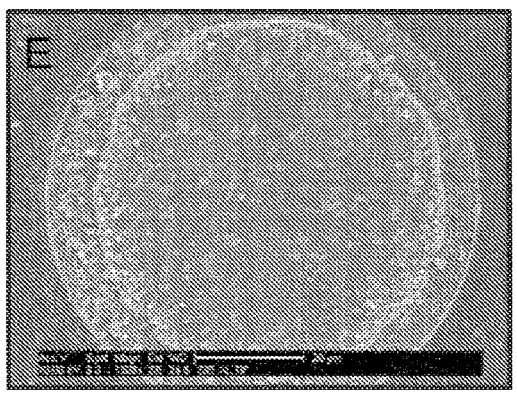
Figure 25F:
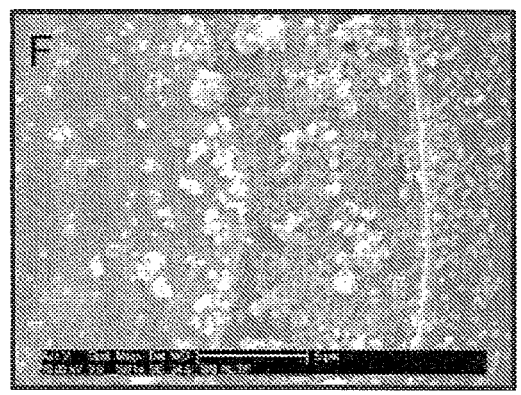
Figure 25G:
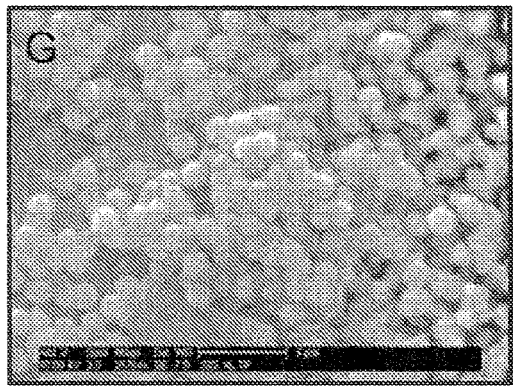
Figure 25H:
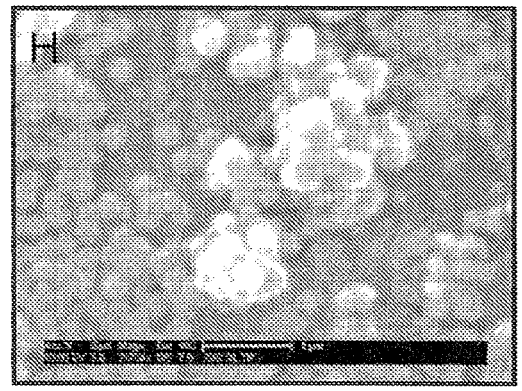

Similar DEP examples were carried out in high conductance 1×PBS buffer with the 200 nm nanoparticles present. FIG. 25A first shows SEM images of the un-activated control microelectrode after two minutes of DEP at 3000 Hz, 10 volts pk-pk in high conductivity 1×PBS buffer. The control microelectrode with no activation shows only a few 200 nm nanoparticles randomly distributed over the structure. FIG. 25B shows a higher magnification SEM image of the edge of a control microelectrode, where some nanoparticles appear randomly trapped in the area between the edge of the platinum microelectrode. FIG. 25C shows the SEM image of a microelectrode, which was activated for 2 minutes with 200 nm nanoparticles present. A large number of nanoparticles have concentrated and adhered to the microelectrode, especially at the edges. The close-up image (FIG. 25D) shows much better the concentrated clusters of nanoparticles and indicates some degradation of the platinum at the edge of the microelectrode. FIGS. 25E and 25F now show images of an activated microelectrode after 5 minutes of DEP with 200 nm nanoparticles. Again concentration and clustering of the 200 nm nanoparticles is clearly observed, but the platinum microelectrode structure now appears more severely damaged and degraded. FIG. 25G is a higher magnification SEM image of the edge of the microelectrode from FIG. 25D, again showing clustering of the nanoparticles. Finally, FIG. 25H is a higher magnification image of the degraded microelectrode (seen in FIG. 25F), showing the nanoparticle clusters interspersed with fused or melted clusters of nanoparticles. These fused nanoparticle clusters are the results from the aggressive electrochemical activity (heat, $H^+$ and $OH^-$) at the longer DEP activation times.

Another set of examples involved carrying out the DEP separation and detection of 40 nm red fluorescent nanoparticles from 10 micron spheres in high conductance 1×PBS buffer on microelectrode structures without a hydrogel. FIG. 26A is a red fluorescent image of the microelectrode before DEP activation showing no concentration of the 40 nm nanoparticles. FIG. 26B is the red fluorescent image of microelectrode after DEP activation for 4 minutes at 10,000 Hz, 10 volts pk-pk, which now clearly shows the concentration of 40 nm nanoparticles on the perimeter of the microelectrodes. FIG. 26C is an SEM high magnification image showing the damaged microelectrode and clustering of the 40 nm nanoparticles.

These examples clearly show that increased electrochemical activity is occurring when DEP is carried out under high conductance conditions (>100 mS/m). This very aggressive electrochemistry causes micro-bubbling and darkening of the microelectrodes. More importantly, it shows that significant microelectrode degradation is occurring, which ultimately leads to electrode failure, and it shows that this microelectrode destruction increases as DEP activation time increases. The fact that fusion of the polystyrene nanoparticles was observed on the degraded microelectrode structures suggests that significant heating is occurring, in spite of DEP being an AC electrokinetic process. These results can be attributed to DC electrolysis reactions which would produce $O_2$, $H_2$, $H^+$, $OH^-$, heat and bubbles. The presence of sodium ($Na^+$), potassium ($K^+$), and chloride ($Cl^-$) electrolytes in the 1×PBS buffer may also contribute to overall corrosive conditions present on the microelectrode surfaces during DEP. In addition to high conductance, most biological and clinical samples and buffers have relatively high concentrations of sodium ($Na^+$), potassium ($K^+$), and chloride ($Cl^-$). These results immediately make it clear as to why classical DEP, which utilizes less robust sputtered gold electrodes, could only be carried out at low conductance conditions (Ref. 29, 30), i.e., the electrodes would be destroyed in seconds.

While the hydrogel overcoated platinum microelectrodes do allow separation of nanoparticles at high conductance conditions, they are nevertheless still unsuitable for any practical applications for the following reasons. First, pronounced random bubbling and electrode failure would make the device itself unreliable for any type sample to answer molecular diagnostics using blood. In further experiments involving the separation of nanoparticles from buffy coat and whole blood, bubbling, electrode darkening, and electrode failure were observed. While nanoparticles could be isolated into the high field regions, they were difficult to remove by fluidic washing, indicating adverse heating may have fused them to the array surface. Second, for biological sample separations and subsequent molecular analyses (e.g. PCR, immunoassay, etc.) this heating and aggressive electrochemistry would be severely damaging to cells, DNA, proteins, and most other analytes. Third, in order to improve the separation efficiency (increase the total amount of analyte concentrated), longer DEP times would be required, which would produce even more adverse effects. Fourth, if higher AC voltages (e.g. 20 volts pt-pt) are used to increase concentration speed, this would also cause even more bubbling and electrochemistry effects. This discovery of the underlying reasons for classical DEP device and conductance limitations now provides the opportunity to create more viable DEP sample preparation devices and novel "seamless" sample-to-answer diagnostic systems. These novel DEP devices will allow rare cells, nanoparticles, and a variety important disease biomarkers to be directly isolated, concentrated, and detected in blood, plasma, serum, and most other biological samples and buffers.

This description next discloses a combination of continuous and/or pulsed electrokinetic/dielectrophoretic (DEP) forces, continuous and/or pulsed DC electrophoretic forces, on-device (on-array) microelectrophoretic size separation, and controlled fluid flow (externally pumped and/or DC/AC electrokinetic driven) together with the novel devices of this invention that can be used to carry out complex sample preparation, leading to specific analyte separation and concentration, and subsequent molecular diagnostic analyses and detection. This can include but is not limited to (1) both the DEP separation and detection of labeled analytes and/or the subsequent detection of unlabeled analytes after DEP separation, using immunochemistry and ligand binding techniques that include fluorescent antibodies, non-fluorescent antibodies, antibody derivatized nanoparticles, antibody derivatized microspheres, antibody derivatized surfaces (specific sites on the DEP device), biotin/strepavidin, and various lectins; (2) the pre-DEP or post-DEP use of general and/or specific color stains, fluorescent dyes, fluorescent nanoparticles, quantum dots for detecting specific cells, bacteria, virus, DNA, RNA, nuclei, membranes, cellular organelles, and cellular nanoparticulates (it is important to keep in mind that DEP is intrinsically a "label less" technique and that cells, nanoparticles, and other analytes can be identified by their cross-over frequencies; labeling is used to increase detection sensitivity, identify individual entities, and carry out more detailed analysis); and (3) the post analysis of cells, nuclei, DNA, and RNA by fluorescent probe in-situ hybridization (FISH, etc.); and (4) use of well-known molecular analysis methods for cells, nuclei, DNA, and RNA including but not limited to PCR, RCA, SDA, and other genotyping, sequencing, and gene expression techniques-all of which can be carried out in the same chambered compartment in which the DEP separation has occurred.

The above examples do not exclude carrying out subsequent analyses in another separate chamber of the device or moving the analytes to a sample collection tube(s) for off-device analyses, storage, or archiving of samples. Additionally, other types of detection techniques that can be used for analysis include, but are not limited to, radioisotopes, colorometric, chemiluminescence, electrochemical, or other methods for biosensing or nanosensing of the analytes, biomolecules, and cells once they have been isolated. The devices and processes described herein can be considered a truly "seamless" sample-to-answer diagnostic system that can be used directly with undiluted blood or other complex clinical or biological samples. The seamless sample-to-answer process using the exemplary DEP devices herein are described below in more detail.

Figure 27:
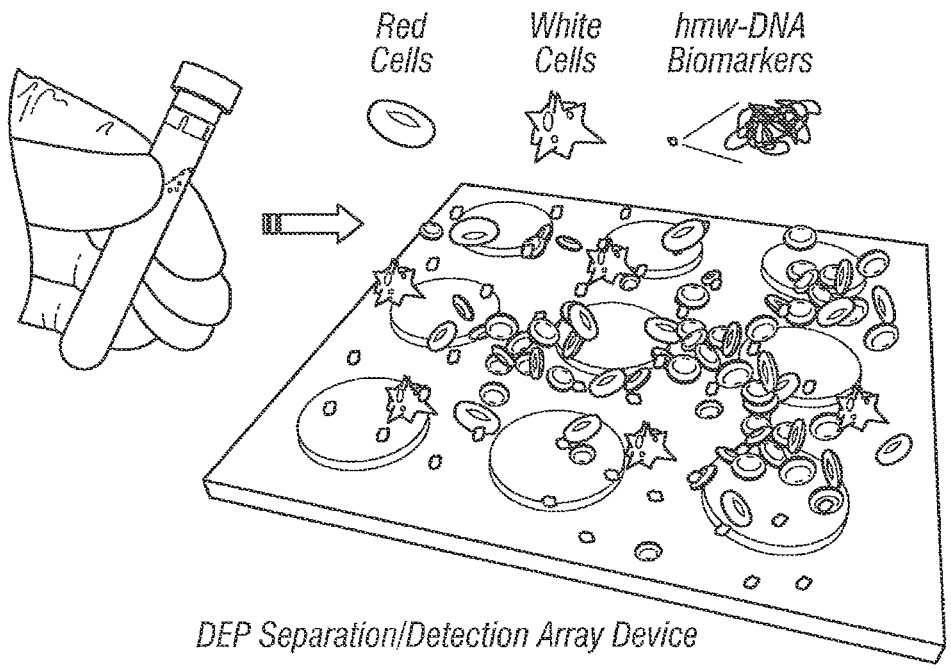
FIG. 27 shows a seamless sample-to-answer hmw-DNA process in blood comprising step 1.

FIG. 27 shows the first step in seamless sample-to-answer diagnostics where a blood sample is applied directly to the device and DEP is used to carry out, in this case, the separation of a very low concentration of high molecular weight (hmw) DNA and/or RNA from the un-diluted whole blood sample. It should be noted, however, that almost any analyte including but not limited to rare cells, nanoparticles, cellular nanoparticulates, antibodies, immunocomplexes, proteins, and RNA could be separated, concentrated, and detected; and samples could include but are not limited to plasma, serum, urine, and saliva.

Figure 28:
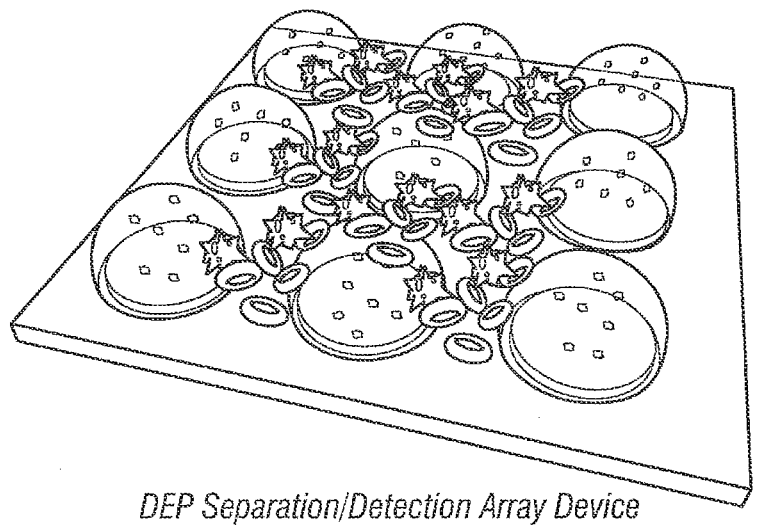
FIG. 28 shows a seamless sample-to-answer hmw-DNA process in blood comprising step 2.

FIG. 28 shows the second step in a sample-to-answer diagnostics process where the DEP field is now applied at the proper AC frequency and voltage that causes the blood cells (red and white) to move to negative (DEP) low field regions, and the hmw DNA (RNA) to concentrate into the positive (DEP) high field regions (in the drawing, dome structures represent the DEP high field strength areas).

Figure 29:
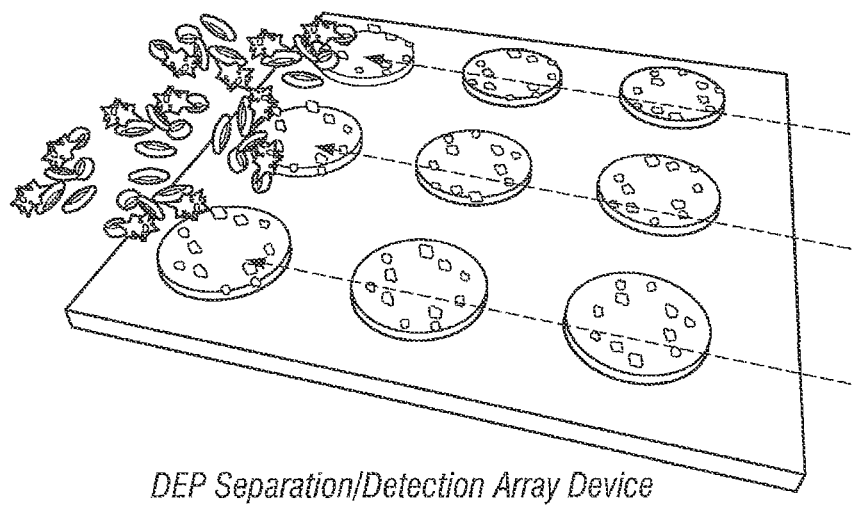
FIG. 29 shows a seamless sample-to-answer hmw-DNA process in blood comprising step 3.

FIG. 29 shows the third step, where a simple fluidic wash is used to remove the blood cells from the DEP array device, while the hmw-DNA (RNA) remains highly concentrated in the DEP high field regions. It is also within the scope of this disclosure to use a continuous, pulsed, or intermittent fluidic flow across the DEP device in order to process a larger sample volume, and as a mechanism to reduce heating, which is more pronounced in higher conductance solutions, at lower AC frequencies (<20 kHz), and at high voltages (>20 volts pt-pt).

Figure 30:
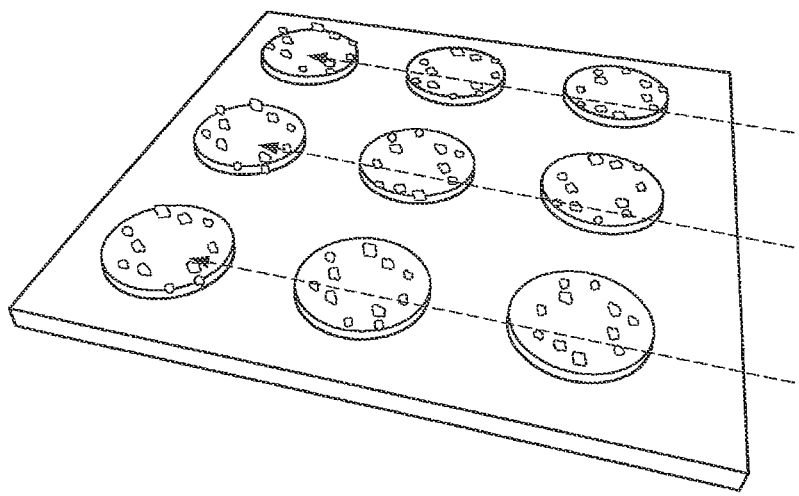
FIG. 30 shows a seamless sample-to-answer hmw-DNA process in blood comprising step 4.

FIG. 30 shows the next step in the process, which involves the in-situ labeling of the DNA (RNA) by addition of a DNA (RNA) specific fluorescent dye (e.g. CyberGreen, OliGreen, ethiduim bromide, TOTO, YOYO, acridine orange, etc.). In this process, a solution of the appropriate fluorescent dye is flushed across the DEP device to stain the DNA or RNA. The DNA/RNA can be held in place by maintaining the DEP field while staining is in progress. The fluorescent stained DNA/RNA can now be detected and quantified by using an epifluorescent detection system (FIG. 31). Fluorescent detection systems and devices are well-known in the art of molecular biology and clinical diagnostics for analysis of microarray devices, and a variety of systems are commercially available.

It is also within the scope of this disclosure to: (1) use other molecular analysis detection methods and techniques including but not limited to PCR, real time PCR with molecular beacons, RCA, and SDA; (2) to hybridize the sample DNA/RNA during the DEP separation process to capture probes (DNA, RNA, pNA, etc) immobilized to specific sites on the DEP device for subsequent analysis/detection using fluorescent reporter probes; (3) to release the DNA/RNA from the DEP concentration sites, amplify it using PCR, RT-PCR, RCA, or SDA, denature and then use site-selective DC electrophoresis to re-hybridize the ampl icons to capture probes immobilized on the DEP device for subsequent analysis/detection using fluorescent reporter probes; (4) to use fluorescent in-situ hybridization with sequence specific DNA/RNA/pNA probes; (5) to release the DNA/RNA and transport it either by DEP or electrophoretically (DC fields) to another specific location on the device; and (6) to release the DNA/RNA and move it (by fluid flow) to another chamber of the device or to a sample collection tube for further analysis or storage.

FIG. 32 shows how the sample-to-answer device can be used to carry out more multiplex DEP separation of rare cells, bacteria, virus, cellular nanoparticulates, or CNPs (cellular membrane, nuclei, hmw-DNA, hmw-RNA, vacuoles, endoplasmic reticulum, mitochondria, etc.), proteins, antibody complexes, and other biomarkers from whole blood. FIG. 33 shows the molecular analyses methods that can now be used to identify the specific analytes that have been concentrated onto the device; these methods include but are not limited fluorescent staining, fluorescent immunoassay, FISH, and PCR, RCA, and SDA procedures. Finally, FIG. 34 shows the final detection of cells, bacteria, virus, CNPs, and antibody complexes using well-known fluorescent and other detection techniques.

This disclosure further describes unique methods that can be used to enhance the analytical and diagnostic capability of the sample-to-answer devices and systems described herein. In the case of DNA and RNA isolation and detection, while DEP can be used to efficiently isolate and concentrate hmw-DNA/RNA, lower molecular weight DNA and RNA (<10 kb) are more difficult to isolate by DEP. In this case, double-stranded ds-DNA specific antibodies and single-stranded ss-DNA specific antibodies are available that can be used to label the lower molecular weight DNA and RNA, creating larger nanostructures (>5 nm). These larger DNA-antibody complexes can be more efficiently isolated and concentrated by DEP.

Additionally, a variety of new antibody tests can be enabled using the devices described herein. More specifically, the ability of DEP to separate single antibodies form larger antibody complexes means that numerous single and double antibody assays can be developed in which the formation of the larger antibody-antigen complex can be separated from the clinical sample by DEP. In these cases, fluorescent antibodies and/or secondary antibodies could be added directly to the sample, DEP is applied, and only the fluorescent labeled antibody-antigen complexes would be concentrated into the DEP high field regions for subsequent detection. Such DEP based antibody assays can be used for small molecule antigens including but not limited to drugs, hormones, metabolites, and peptides; as well as for larger antigens including but not limited to proteins, enzymes, and other antibodies. It is also in the scope of this description to enable many other similar DEP assays that are based on the formation of larger complexes, including but not limited to detection of bacteria, virus, bacteriophage, nanoparticles, CNP's using selective ligand binding with antibodies, biotin/streptavidin, lectins, proteins, enzymes, peptides, dendrimers, apatamers, quantum dots, fluorescent nanoparticles, carbon nanotubes, and other nanoentities designed for selective labeling an detection purposes. Finally, In addition to attaching or immobilizing DNA/RNA/pNA capture probes on the DEP device, a variety of other binding entities can be also be attached to the DEP device, including but not limited to antibodies, biotin/streptavidin, lectins, proteins, enzymes, peptides, dendrimers, and apatamers. Such immobilized ligands will provide for selective binding of analytes to the DEP device after the DEP field has been turned off.

It should be noted that the novel DEP devices described herein now enable all these methods by the fact that these new DEP devices eliminate or greatly reduce the adverse bubbling, heating, and electrochemistry effects that would otherwise damage or destroy most of the biomolecules (e.g. DNA, RNA, antibodies, proteins, etc) that are used for immobilization, as well as the analytes and biomarkers being isolated and concentrated on specific DEP high field sites on the device for detection and analyses.

This first specification discloses in more detail novel electrokinetic DEP devices and systems in which the electrodes are placed into separate chambers and positive DEP regions and negative DEP regions are created within an inner sample chamber by passage of the AC DEP field through pore or hole structures. Various geometries can be used to form the desired positive DEP (high field) regions and DEP negative (low field) regions for carrying cell, nanoparticle and biomarker separations with the sample chamber. Such pore or hole structures can be filled with a porous material (agarose or polyacrylamide hydrogels) or be covered with porous membrane type structures (paper, cellulose, nylon, etc). Such porous membrane overlaying structures can have thicknesses form one micron to one millimeter, but more preferably form 10 microns to 100 microns; and pore sizes that range from one nanometer to 100 microns, but more preferably from 10 nanometers to one micron. By segregating the electrodes into separate chambers, these unique DEP devices basically eliminate any electrochemistry effects, heating or chaotic fluidic movement from influencing the analyte separations that are occurring in the inner sample chamber during the DEP process. These chambered devices can be operated at very high AC voltages (>100 volts pt-pt), and in addition to DEP they could also be used to carry out DC electrophoretic transport and electrophoresis in sample chamber. In general these devices and systems can be operated in the AC frequency range of from 1000 Hz to 100 mHz, at voltages which could range from 1 volt to 2000 volts pt-pt; and DC voltages from 1 volt to 1000 volts, at flow rates of from 10 microliters per minute to 10 milliliter per minute and in temperature ranges from 1° C. to 100° C. The chambered devices are shown in FIG. 1 and FIG. 2. Such devices can be created with a variety of pore and/or hole structures (nanoscale, microscale and even macroscale) and may contain membranes, gels or filtering materials which can control, confine or prevent cells, nanoparticles or other entities from diffusing or being transported into the inner chambers. However, the AC/DC electric fields, solute molecules, buffer and other small molecules can pass through the chambers.

FIGS. 1 and 2 represents a most basic version of the chambered devices that can be constructed in accordance with the invention. A variety of configurations are envisioned for the devices in accordance with the invention. Such devices include, but are not limited to, multiplexed electrode and chambered devices, devices that allow reconfigurable electric field patterns to be created, devices that combine DC electrophoretic and fluidic processes; sample preparation devices, sample preparation and diagnostic devices that include subsequent detection and analysis, lab-on-chip devices, point-of-care and other clinical diagnostic systems or versions. FIG. 1 is a schematic diagram of a sample processing device constructed in accordance with the teachings herein, and shows that the device 100 includes a plurality of electrodes 102 and electrode-containing chambers 104 within a housing 106. A controller 108 of the device independently controls the electrodes 102, as described further herein.

FIG. 2 shows a top view of a the device 100 which is illustrated with six electrode chambers 104, each of which has at least one robust platinum electrode. FIG. 2 shows the device configured with one main central separation chamber 110, which has an arrangement of eighteen pore/hole structures 112 of varying size that are filled with a hydro-gel (the inner chamber could also have a porous membrane covering the pores or holes). The pore/hole structures are arranged in three groups of six pore/hole structures. While the upper part of the separation chamber 110 has no physical separations, the lower portion is divided into nine separate compartments (indicated by the light dashed line). Each of these compartments is in fluidic contact with an electrode chamber, but not with each other. When an AC DEP field is applied to the electrodes, the field passes through the pores 112, creating positive DEP high field regions on top of the pore structures and negative DEP low field regions between the pore structures. Samples can be added and removed from the device via the inlet 220 and outlet 222. The device may additional inlets 224 and outlets 226. The device shown in FIGS. 1 and 2 represents just one form of a high conductance DEP chambered device; it should be understood that a large number of different types of devices with larger numbers of pores/holes and different geometries can be created.

Another device embodiment involves using electrode arrays with robust electrodes of defined diameter and separation distances that will allow for less electrochemical effects and heating, which is a problem in current electrokinetic and dielectrophoretic separation devices. Proper construction and overcoating of robust electrodes (e.g. platinum, palladium and gold) can reduce adverse effects of electrochemistry products on the separation process, and allow much higher voltages to be applied, which can greatly improve separation times. Also, current devices are relatively low throughput and this embodiments described herein have overcome that problem by providing a system that uses multiplexed parallel section arrays and that allows the device to be used as one large separation zone and then switched to separately controlled separations zones, resulting in increased sensitivity and selectivity of the overall system. A third problem seen in other conventional systems is the inability to separate sample components that are relatively similar in size and composition. This problem is overcome in accordance with the description herein by providing a device that can carry out secondary separation processes, such microelectrophoresis, directly on the DEP array device itself.

Negative dielectrophoretic (DEP) forces are relatively weaker than positive DEP forces; thus entities that experience negative DEP can be moved by fluid flow, while positive DEP experiencing entities will remain in place. In the presently described embodiments, by using both fluid and DC electrophoretic forces in opposite directions, DNA fragments and highly charged DNA nanoparticulates can be separated from cells and proteins in blood and other samples. In this way, using multiple AC frequencies, pulsed DC electrophoresis, and micro-electrophoresis, a more complete size separation of DNA nanoparticulates and DNA fragments can be accomplished.

Commercial uses of such novel systems and devices that now allow DEP to be carried out under high conductance conditions (blood, plasma, serum, etc.) will likely include numerous research and clinical diagnostic applications, such as point of care diagnostics, therapeutics and drug monitoring, environmental and water supply monitoring, and bioterror agent detection. Numerous analytes and entities such as rare cells (cancer cells, fetal cells, hematopoietic stem cells), bacteria, virus, DNA/RNA, and DNA nanoparticulate biomarkers, drug delivery nanovesicles, as well as normal or aberrant proteins, might be detected using such a system.

An experimental AC DEP and DC electrophoretic separation system (a laboratory bench-top version described further in the Experimental Section below) has been built and experiments were conducted to refine the new prototype devices. The results obtained on these devices (which are described above) lead to the important discovery as to why classical DEP has been limited to low conductance solutions.

Now new devices that use planar, parallel, and robust platinum electrode arrays with electrodes of roughly about 1-1000 micron in diameters with 10 to 5000 micron separation distance and overcoated with a 5-100 micron thick hydrogel (agarose, polyacylamide) or porous membrane layer(s), allows for less heating and electrochemistry issues, as the electric field lines are not as highly concentrated as they are in other classical conventional DEP systems, and more importantly the DEP high field accumulation region is actually now some distance from the actual electrode surface. One significant difference from previous electrode designs is not using sputtered platinum or gold electrodes, which are easily degraded and destroyed by electrochemistry, particularly at higher field strengths and high solution conductance. The electrodes for the new devices will be constructed from solid platinum or gold materials, including wires or rods. A second difference is that the separation efficiency for isolating one unique entity in a million relatively similar entities (cells, nanoparticles, biomarkers) can be improved by changing the problem of one large separation to that of many separate separations which are much more controllable. The devices described herein accomplish this by using multiplexed sectioned arrays and a controlled parallel sorting process. This is achieved by using individually controlled array subsets of 10 to 100 or more electrodes in a large array device that allows a complex biological sample (blood) to be distributed across the array device, separating the components into smaller separation sections (areas) for further separation and isolation of the desired analytes or entities. Breaking the complex sample separation problem down into smaller parts holds the most promise for solving the issue of sensitivity versus specificity, i.e., the process allows both rapid and higher overall sample throughput, as well as relatively longer interrogation (separation) times for isolating and identifying unique cells or other entities in the sample. Finally, the last problem can be overcome by creating a multi-dimensional hierarchical sorting device. This solution relies on the fact that negative DEP is a weaker force than positive DEP and cells or other entities experiencing negative DEP can be moved by controlled fluid flow, whereas the positive DEP experiencing analytes or entities will stay concentrated in the DEP high field areas. Through the use of controlled fluid flow and pulsed DC electrophoresis in opposite directions, DNA/RNA and charged nanoparticulates can be separated from cells and proteins in a complex biological sample (this is in addition to the intrinsic ability of DEP to separate cells and DNA).

Combining controlled fluid flow and pulsed DC electrophoresis with using multiple AC frequencies, i.e. low frequency to trap the CNPs and hmw-DNA/RNA nanoparticulates in on the initial electrodes array subset, and higher AC frequencies on other electrode array subsets to trap cells progressively larger particles (bacteria and virus) a complete separation of most of the cells and entities by size can be obtained. If desired the electrodes can be switched to different frequencies for finer separation to occur locally while globally the overall size separation is maintained.

We describe a separation system involving a device with planar, robust, platinum electrode array structures and auxiliary electrodes, into which a complex biological sample (blood, plasma, serum) is directly applied, such that controlled AC signals from one or more function generators produce dielectrophoretic forces, and a controlled DC power supply produces electrophoretic forces. The inlet and outlets of the device also allow for the controlled passage of fluids (water, buffers, etc.) through the system at a controlled flow rate. The system also includes an optical/epifluorescent microscope and digital camera for monitoring, detecting, quantifying, and recording the separation processes that are occurring on the device (visual and fluorescent). The device is ultimately a multiplexing, parallel hierarchical sorting system that is enabled by controlling electrokinetic effects, dielectrophoretic forces, electrophoretic forces, microelectrophoresis, and fluid flow. It should be noted that such novel multiplex sample-to-answer processes are made possible by the fact that the new DEP devices eliminate or greatly reduce the adverse bubbling, heating, and electrochemistry effects experienced by conventional devices.

Figure 3:
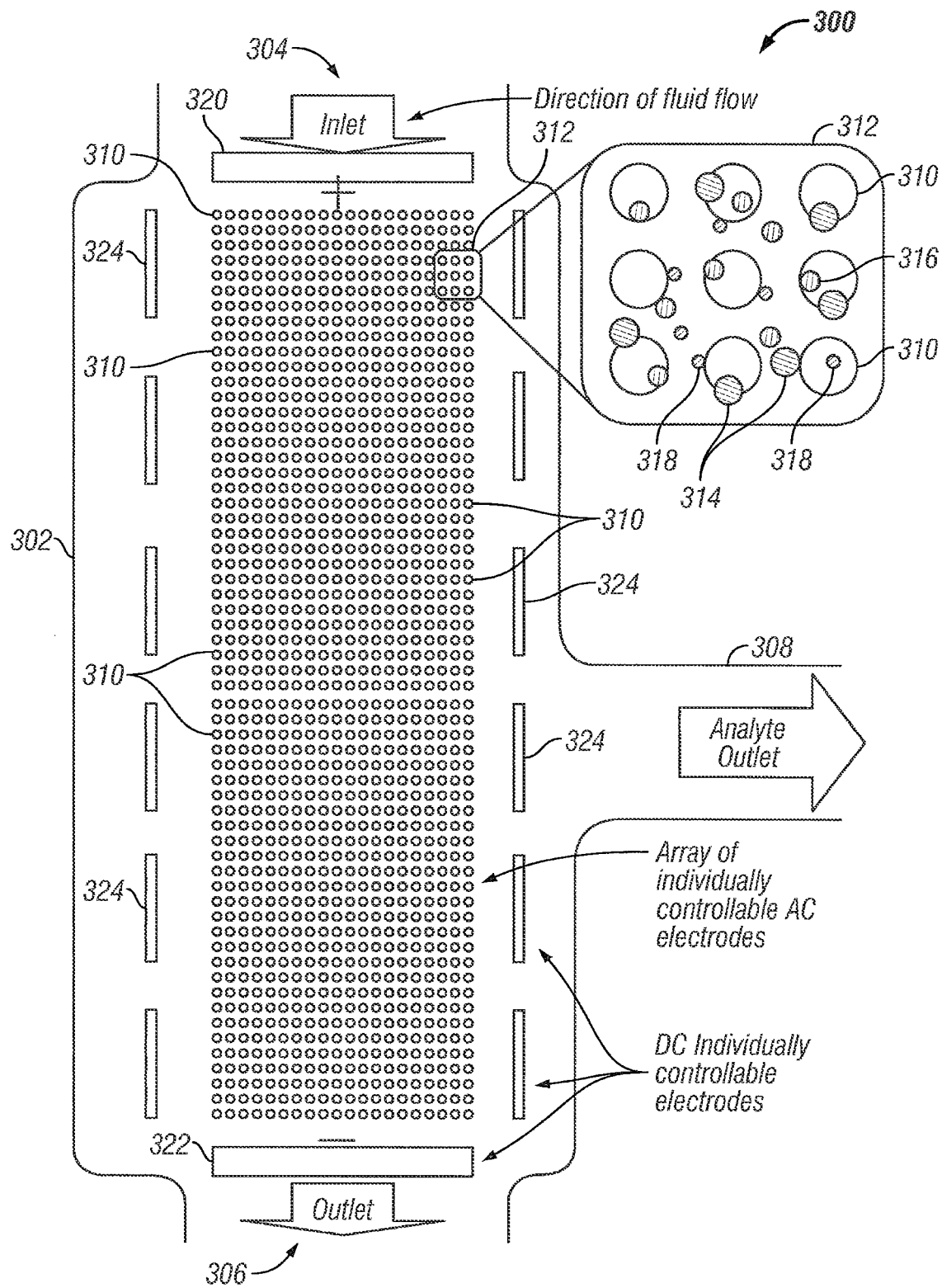
FIG. 3 shows an electrode arrangement constructed in accordance with the invention, with an exemplar fluid flow and sample indicated.

FIG. 3 shows just one version of a planar platinum electrode array device 300 comprising a housing 302 through which a sample fluid can flow. The fluid flow pattern through the device is indicated by the large arrows, representing flow of an idealized sample, from an inlet end 304 at the top of the drawing to an outlet end 306 at the bottom, and a lateral analyte outlet 308. The device includes multiple AC electrodes 310. Only a few of the electrodes 310 are identified in FIG. 3, for simplicity of illustration, but it should be understood that all the small open circles in the drawing figure represent electrodes of similar construction. One enlarged 3×3 array 312 of the electrodes is illustrated on the right side of the drawing figure to show a sample fluid in the device 300. The sample consists of a combination of micron-sized entities or cells 314 (the largest filled-in circles shown in the enlarged view), larger nanoparticulates 316 (the intermediate-sized filled-in circles) and smaller nanoparticulates or biomolecules 318 (the smallest-sized circles). The larger nanoparticulates 316 could represent high molecular weight DNA, nucleosomes, or CNPs or cellular debris dispersed in the sample. The smaller nanoparticulates 318 could represent proteins, smaller DNA, RNA and cellular fragments. The planar electrode array device 300 in the figure is a 60×20 electrode array that can be sectioned into three 20×20 arrays that can be separately controlled but operated simultaneously. The auxiliary DC electrodes 320 at the top of the figure can be switched on to positive charge, while the DC electrodes 322 at the bottom of the figure are switched on to negative charge for electrophoretic purposes. Each of the controlled AC and DC systems can be used in both a continuous and/or pulsed manner (e.g., each can be pulsed on and off at relatively short time intervals). The planar electrode arrays 324 along the sides of the sample flow, when over-layered with nanoporous materials, can be used to generate DC electrophoretic forces as well as AC DEP. Additionally, microelectrophoretic separation processes can be cared out within the nanopore layers using planar electrodes in the array and/or auxiliary electrodes in the x-y-z dimensions. In general these devices and systems can be operated in the AC frequency range of from 1000 Hz to 100 mHz, at voltages which could range from approximately 1 volt to 2000 volts pk-pk; at DC voltages from 1 volt to 1000 volts, at flow rates of from 10 microliters per minute to 10 milliliter per minute, and in temperature ranges from 1° C. to 100° C. The controller 108 (FIG. 1) independently controls each of the electrodes 310, 320, 322, 324. The controller may be externally connected to the device 100 such as by a socket and plug connection (not illustrated), or can be integrated with the device housing. Electrical lead lines for the electrodes are not shown in the drawings, for simplicity of illustration.

It can be assumed that the cells and particles and other entities in the sample are evenly distributed throughout the electrode array, though only the enlarged 3×3 electrode section 312 is shown in the drawing figure. The fluid flow rate is such that it exerts a force stronger than the negative DEP that the larger particles experience, but weaker than the positive DEP that the larger particles experience.

Figure 4:
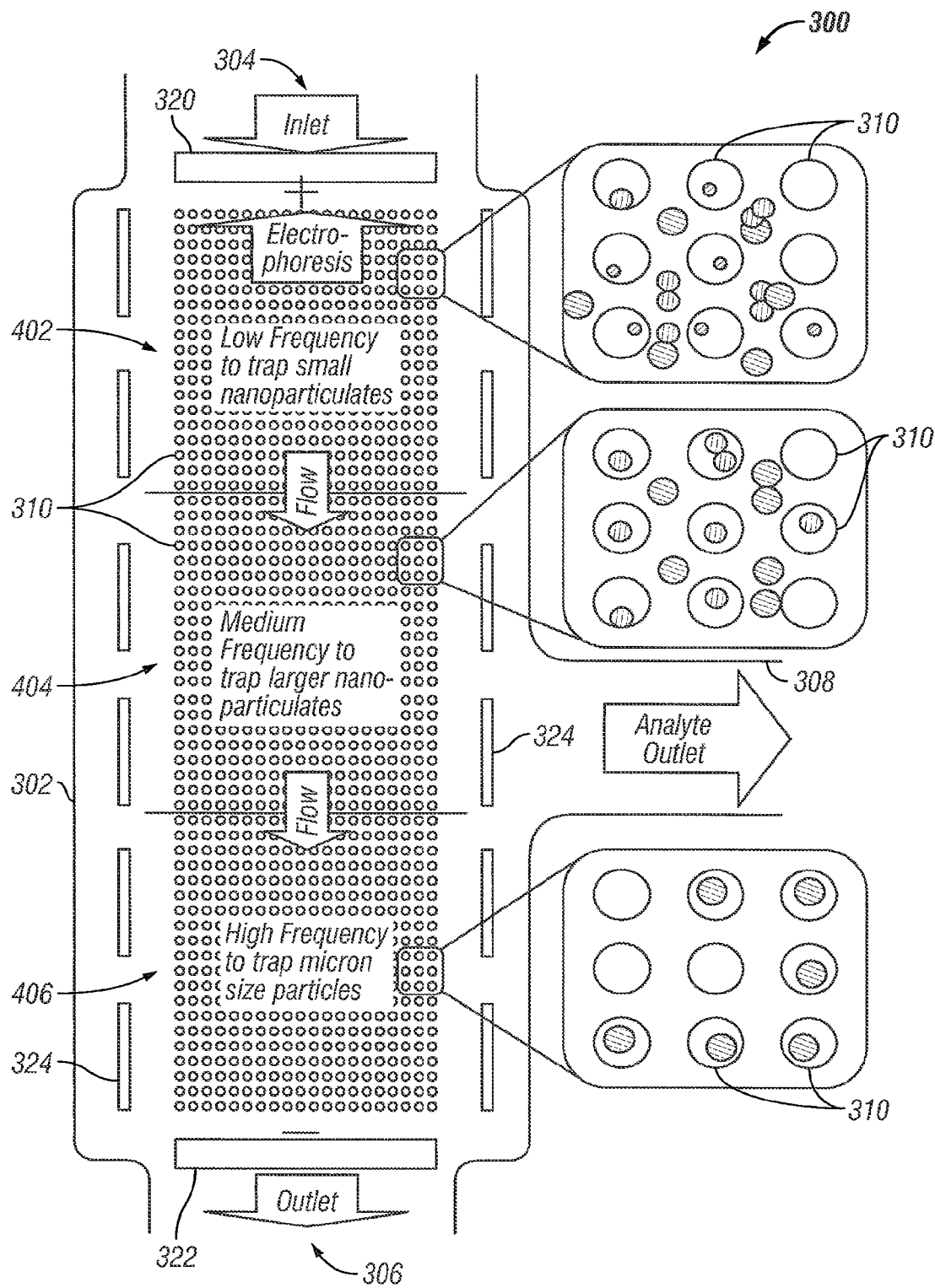
FIG. 4 illustrates the electrode arrangement of FIG. 1 with electrode pulsing in accordance with the invention.

FIG. 4 shows the top 320 and bottom 322 DC electrodes being pulsed on and off (one second on followed by one second off), thereby providing a brief electrophoretic pulse pushing the DNA, RNA, and small nanoparticulates toward the positive DC electrode 320, which is located at the top of the drawing figure. The 60×20 electrode array is visualized as broken into three distinct sections or sub-arrays that are independently controlled. The top twenty AC electrode array rows 402 are tuned to a lower frequency AC field to ensure that the smaller entities, which generally move toward the electrodes, due to positive DEP and AC electrokinetic phenomena at lower frequencies, will be trapped at those electrodes while the larger cells and entities experience negative DEP at these frequencies, and are therefore moved to the lower section of the device by the constant fluid flow. The middle twenty rows 404 of AC electrodes will hold the large sub-micron particles (e.g. virus) while allowing the micron-sized particles and cells to flow though. Finally, the last twenty rows 406 of AC electrodes can be attuned, if desired, to a high AC frequency, which can then be used to capture desired cells and micron-sized particles.

Figure 5:
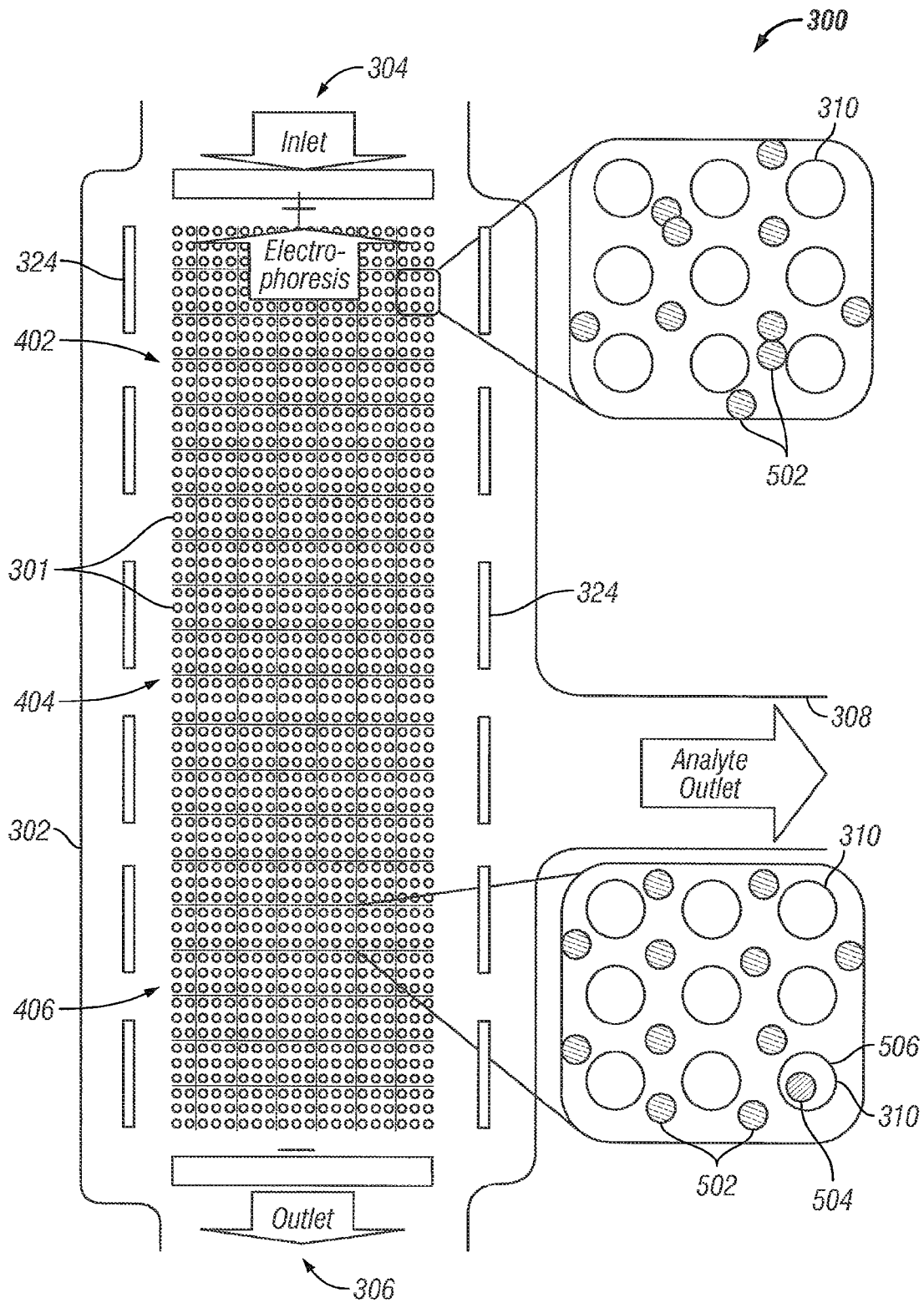
FIG. 5 shows the electrode arrangement of FIG. 1 with selective activation of electrodes to achieve to achieve better separation results.

FIG. 5 shows the separation mechanism for isolating "one cell in a million", i.e., rare cell detection. By using the complete electrode array, it is possible to multiplex and parallelize the problem of separation to make it simpler. This can be achieved by merely activating as much of the electrode array as necessary to achieve better separation. By effectively splitting the array into specific separation areas that can be analyzed by optical detection (i.e., epifluorescence), it should be possible to separate out one specific cell experiencing positive DEP from all the cells around it, once all the cells are evenly distributed. In FIG. 5, the intermediate-sized filled-in circles 502 represent 10 μm cells of one specific kind, such as lymphocytes, red blood cells, and the like, and the single filled-in circle 504 shown on the AC electrode 506 of the third section 406 of AC electrodes represents the lone "one cell in a million" of a type different from the others 502 in the sample, which is also the only cell that experiences positive electrophoresis and is therefore easily distinguishable from the other cells. Using only dielectrophoresis, it should be possible to separate out cells of the lone "one cell in a million" 504 type from the undifferentiated 502 cell types. This is more easily accomplished if there are a sufficient number of AC electrodes to spread the separation problem into smaller, more easily separable and analyzable chunks. Once the cell-type separation problem is spread out in such a manner, if only certain sections of the electrode array are analyzed at a time, such as the 3×3 array shown in FIG. 5, it should be possible to find the lone particle 504 of interest. Additionally, temperature control can be effective in allowing more selective and efficient separation of cells (e.g., separation of cancer and stem cells).

Figure 6:
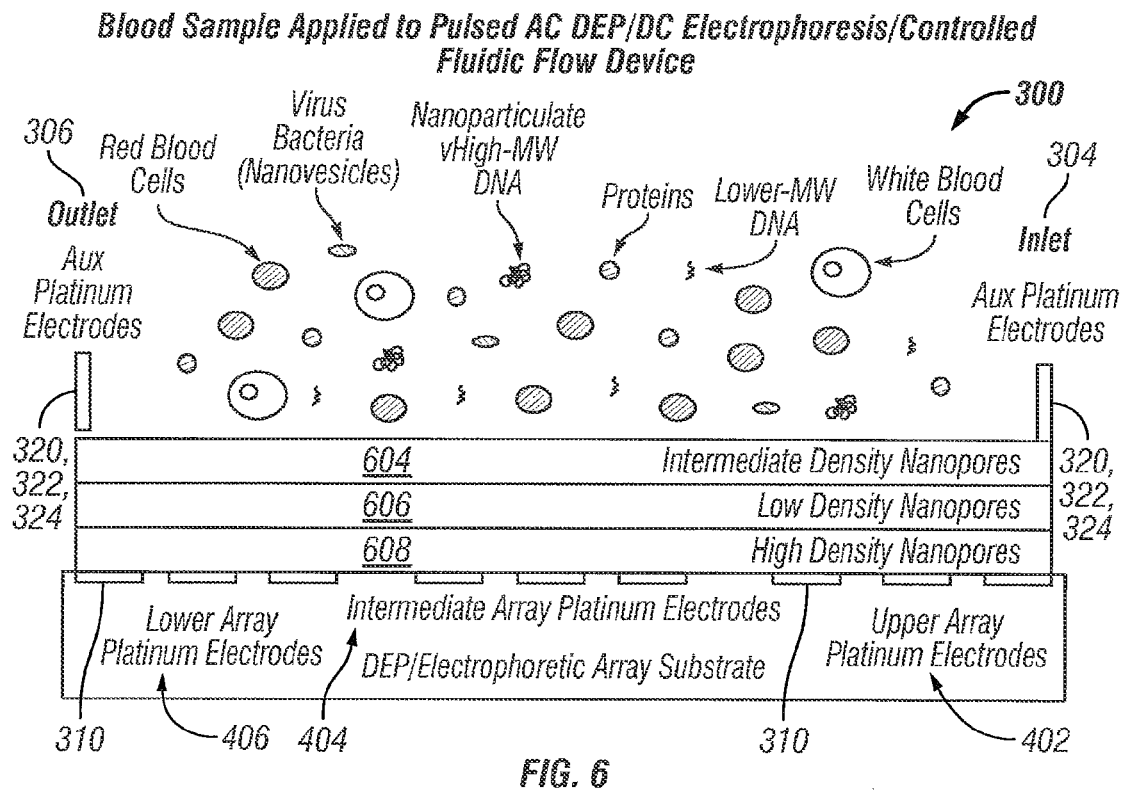
FIG. 6 shows more detailed scheme of blood sample separation process, before combined pulsed AC DEP/DC electrophoresis/controlled fluidic flow are applied.

FIG. 6 shows a more detailed scheme of a blood sample separation process, before the application of combined pulsed AC DEP/DC electrophoresis/controlled fluidic flow. The FIG. 6 diagram shows some of a wide variety of potential diagnostic and biomarker entities that would be found in a complex sample such as blood, which entities may include: red and white blood cells, bacteria, virus, nanovesicles, DNA/RNA nanoparticulates, an assortment of DNA and RNA fragments, and proteins. The FIG. 6 diagram also shows the planar platinum array electrodes 310 covered with an intermediate density nanopore layer 604, a low density nanopore layer 606, and a high density nanopore layer 608 directly over the AC electrodes 310.

Figure 7:
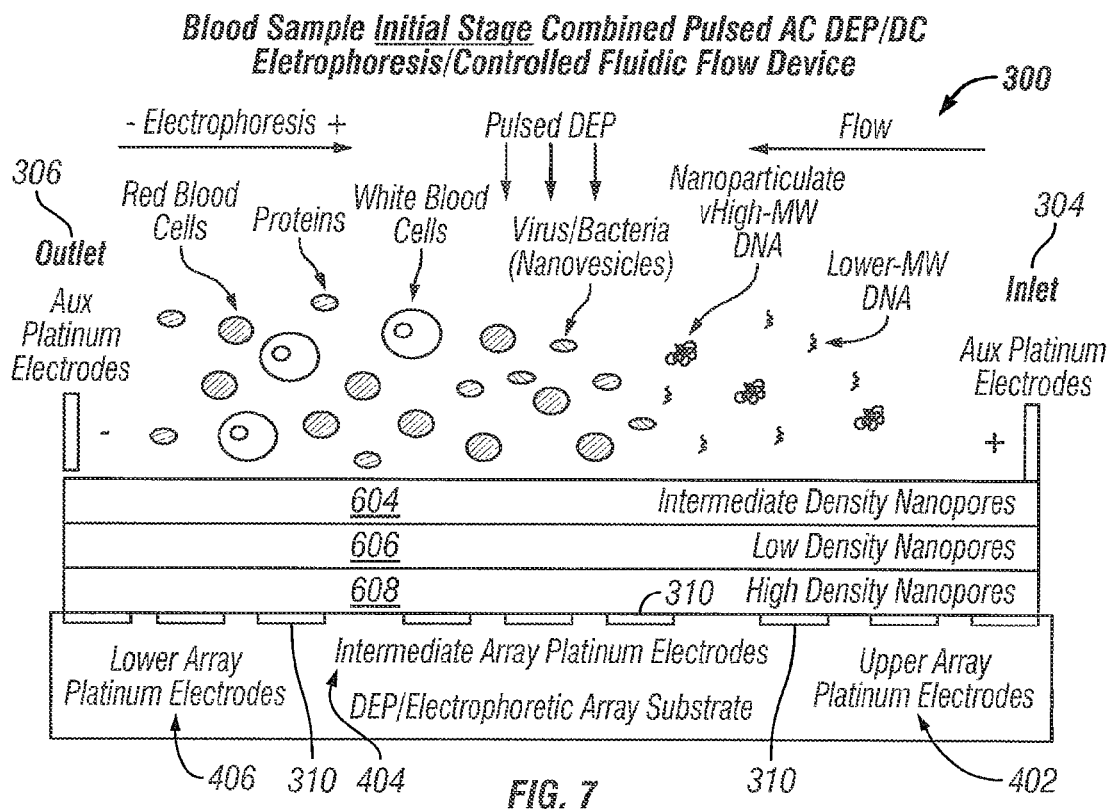
FIG. 7 shows blood sample at initial stage of combined pulsed AC DEP/DC electrophoresis/controlled fluidic flow.

FIG. 7 shows the blood sample in the initial stages of combined pulsed AC DEP/DC electrophoresis/controlled fluidic flow. In FIG. 7, the whole array device 300 is utilized to carry out an overall separation process that begins to concentrate different classes of entities into each of the electrode sub-array sections 402, 404, 406 (upper, middle, lower, respectively).

Figure 8:
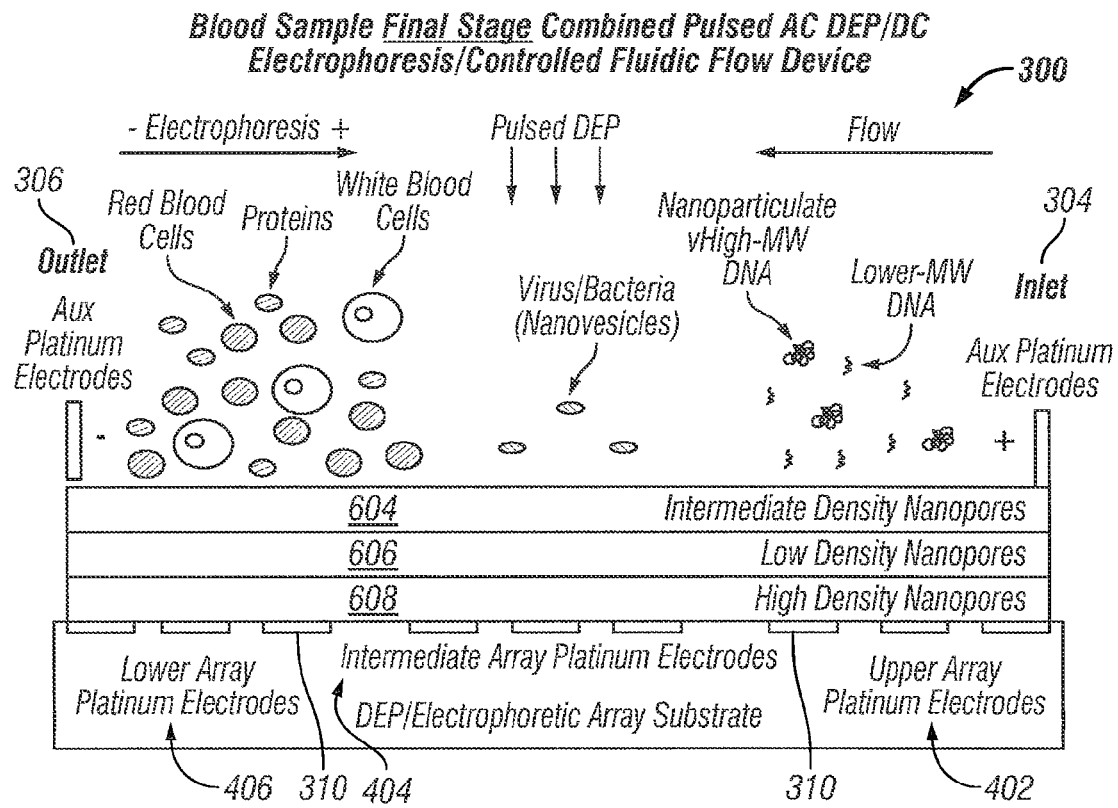
FIG. 8 shows blood sample at final stage of combined pulsed AC DEP/DC electrophoresis/controlled fluidic flow

FIG. 8 shows the blood sample now in final stages of combined pulsed AC DEP, DC electrophoresis, and controlled fluidic flow. In FIG. 8, the different entities have been concentrated into their appropriate electrode array sections 402, 404, 406. In this example, DNA nanoparticulates and smaller DNA fragments are shown in the upper array section 402; bacteria, virus, and nanovesicles are shown in the middle array section 404; and cells and proteins are shown in the lower array section 408.

Figure 9:
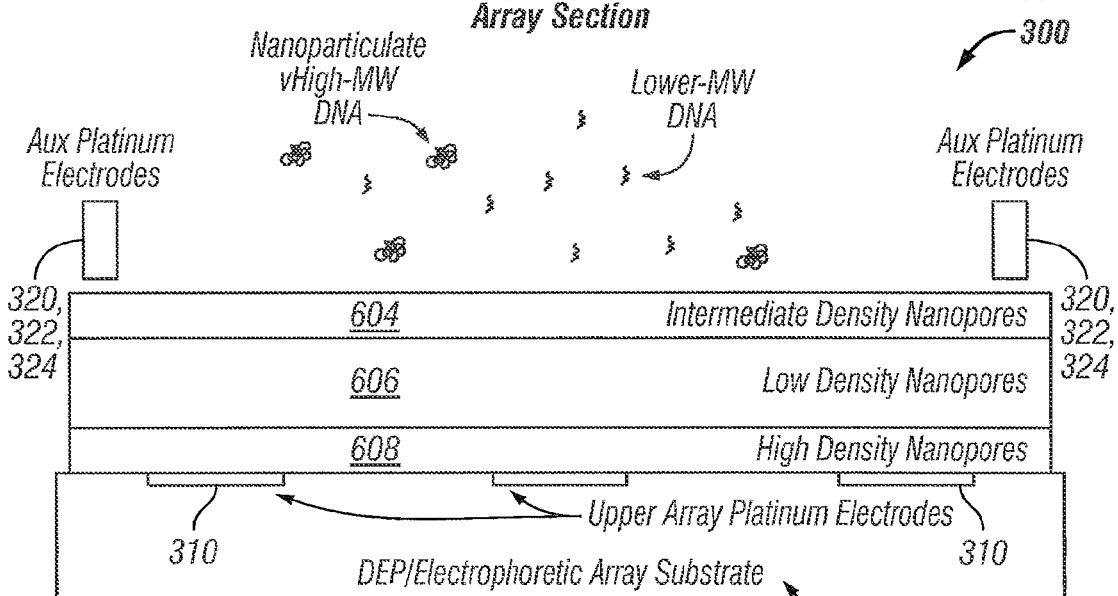
FIG. 9 shows the combined pulsed AC DEP and DC electrophoresis of Fluorescent stained DNA nanopariculates, very high molecular weight DNA and intermediate-lower molecular weight DNA selection and separation on the upper array section.

FIG. 9 shows an enlarged view of the AC electrode array in which the combined pulsed AC DEP and DC electrophoresis of fluorescent-stained DNA nanoparticulates, very high molecular weight DNA and intermediate lower molecular weight DNA selection and separation on the upper array section 402. Because these entities have now been concentrated and isolated in the upper array section they can be selectively stained with appropriate DNA fluorescent dye reagents, and the secondary separation process can now be cared out.

Figure 10:
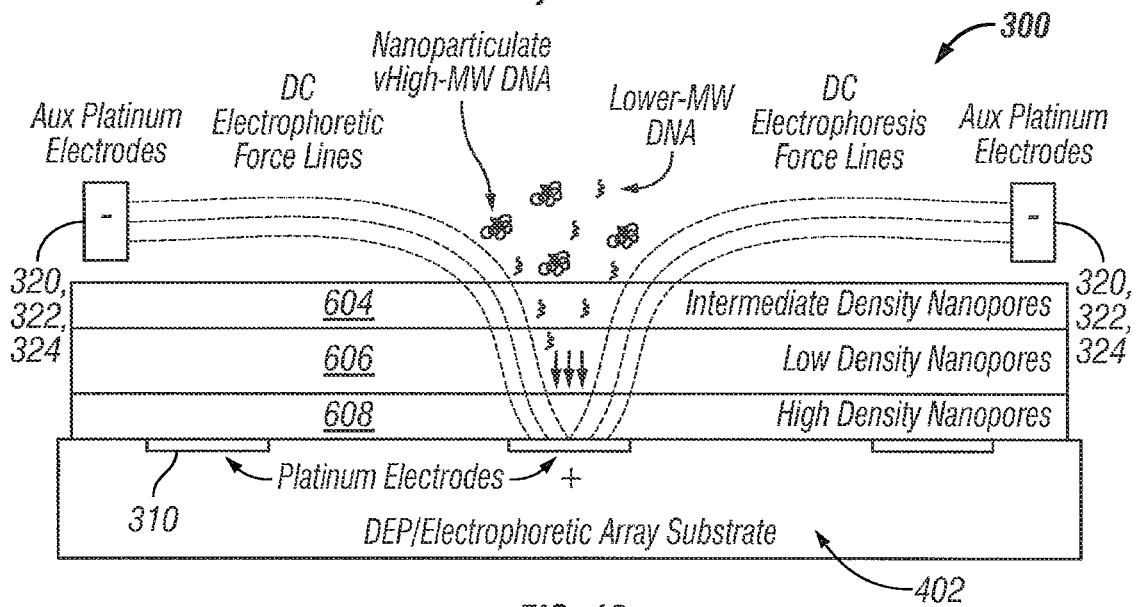
FIG. 10 shows the initial combined pulsed AC DEP and DC electrophoresis of fluorescent stained DNA nanoparticulates, vh MW DNA and intermediate-lower MW DNA selection and separation on upper array section.

FIG. 10 shows the enlarged view of the AC electrode array with initial combined pulsed AC DEP and DC electrophoresis of fluorescent stained DNA nanoparticulates, very high MW DNA and intermediate-lower MW DNA selection and separation on the upper array section 402. This initial process will cause the DNA nanoparticulates to begin to concentrate onto the top of the intermediate nanopore layer which has a pore size that excludes these very large DNA entities; while the more intermediate and lower molecular weight DNA fragments are transported into lower nanopore density layer.

Figure 11:
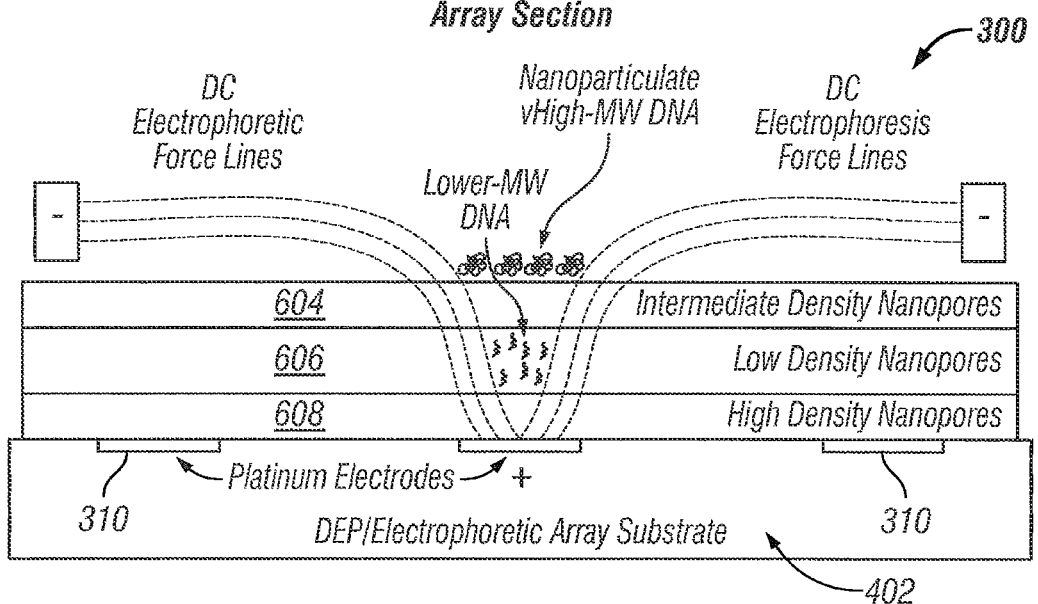
FIG. 11 shows the final combined pulsed AC DEP and DC electrophoresis of fluorescent stained DNA nanopariculates, vh-MW-DNA-and-intermediate-lower MW DNA selection and separation on upper array sections

FIG. 11 shows the enlarged view of the AC electrode array with final combined pulsed AC DEP and DC electrophoresis of fluorescent stained DNA nanoparticulates, very high MW DNA and intermediate-lower MW DNA selection, and microelectrophoresis separation on the upper array section 402. At this point in the operation of the device 300, the DNA nanoparticulates and very high molecular weight DNA are fully concentrated and isolated on the top of the intermediate density nanopore layer 604 and the more intermediate and lower molecular weight DNA fragments are concentrated within the inner lower density nanopore layer 606.

Figure 12:
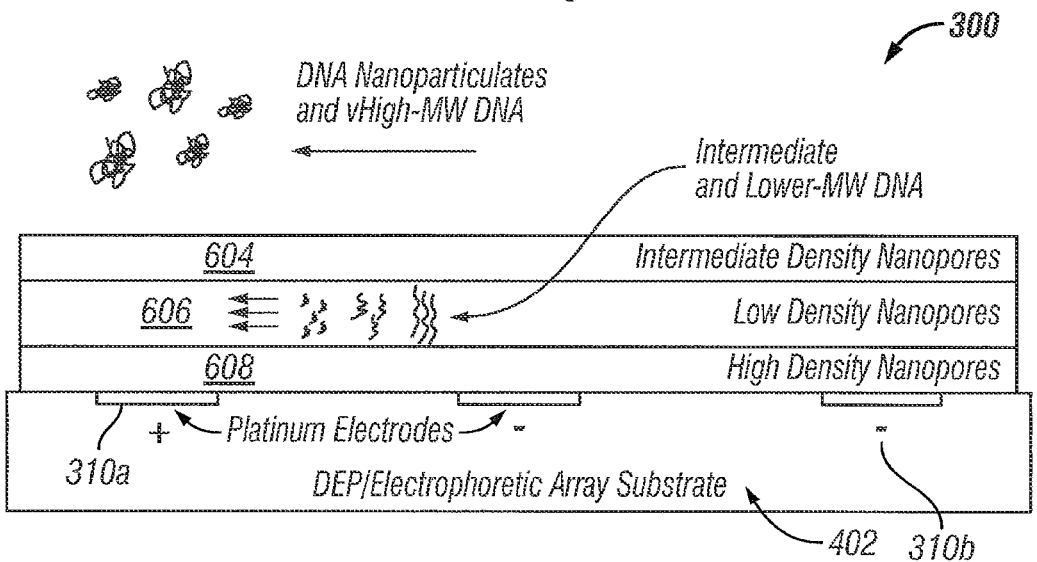
FIG. 12 shows the removal of DNA nanopariculates and very high MW DNA and on-array DC electrophoretic size separation of the intermediate and low MW DNA fragments.

FIG. 12 shows the enlarged view of the AC electrode array 402 after removal of DNA nanoparticulates and very high MW DNA and on-array DC electrophoretic size separation of the intermediate and low MW DNA fragments. The DNA nanoparticulates and very high molecular weight DNA can be further analyzed on another part of the device 300, while the more intermediate and lower molecular weight DNA fragments can be size-separated by microelectrophoresis within the nanopore layers 604, 606, 608. FIG. 12 shows that some of the AC electrodes 310a are positively charged and other AC electrodes 310b are negatively charged.

Figure 13:
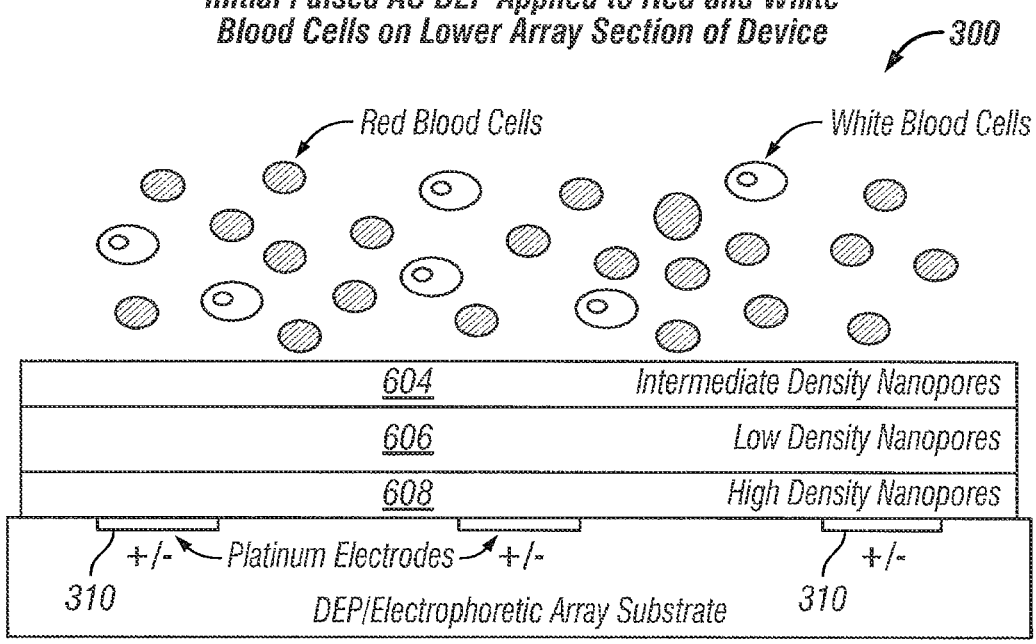
FIG. 13 shows the initial pulsed AC DEP applied to red and white blood cells on lower array section of device.

FIG. 13 shows an enlarged view of the AC electrode array with the initial pulsed AC DEP applied to red and white blood cells on lower array section 406 of the device 300. In this process, the proteins in the sample can be removed and/or analyzed on another component of the device, while the cells and other micron-sized entities can be further separated and differentiated by AC DEP on the lower array section 406.

Figure 14:
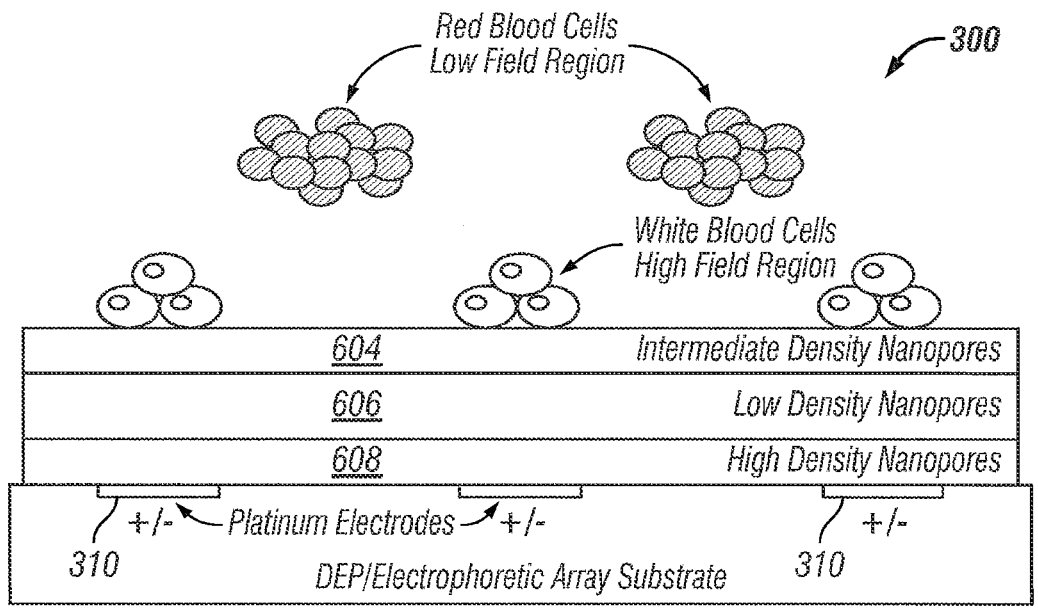
FIG. 14 shows the final pulsed AC DEP applied to red and white blood cells on the lower array section of device.

FIG. 14 shows the enlarged view of the electrode array with the final pulsed AC DEP applied to red and white blood cells on the lower array section 406 of the device 300. At this point of the device operation, the red and white blood cells have been separated in the DEP high and low field regions, subsequently the red cells can be removed and the white cells further differentiated; i.e., begin the process of isolating cancer cells.

Figure 15:
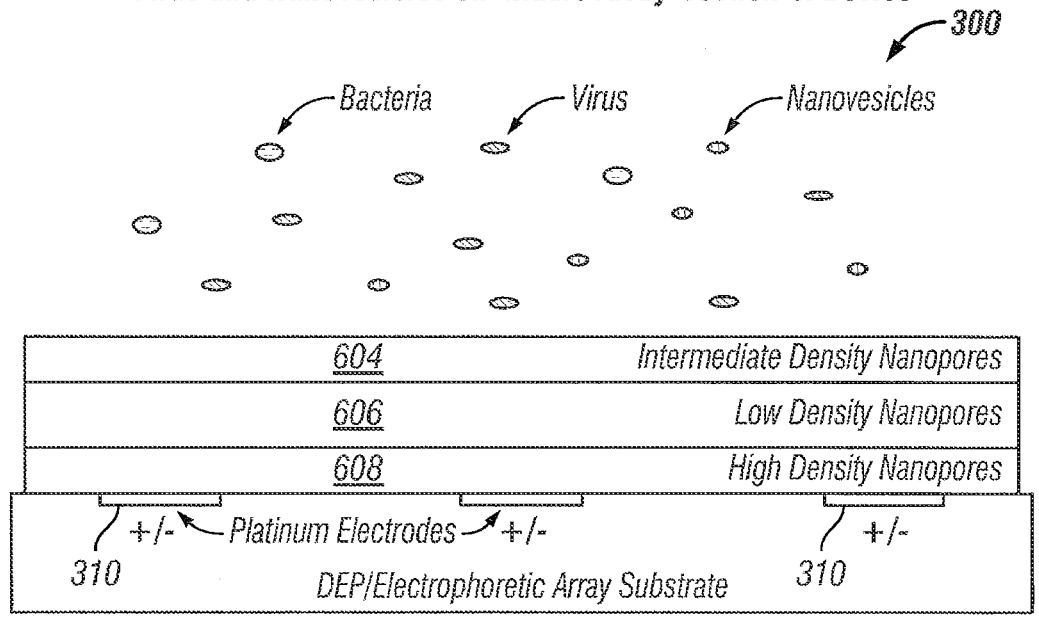
FIG. 15 shows the initial pulsed AC DEP for separation of bacteria, virus and nanovesicles on the middle array section of the device.

FIG. 15 shows an enlarged view of the AC electrode array with the initial pulsed AC DEP for separation of bacteria, virus and nanovesicles on the middle array section 404 of the device 300. The FIG. 15 drawing is an example of how sub-sections of the array device 300 that can be independently controlled can be used to carry out additional important separation processes.

Figure 16:
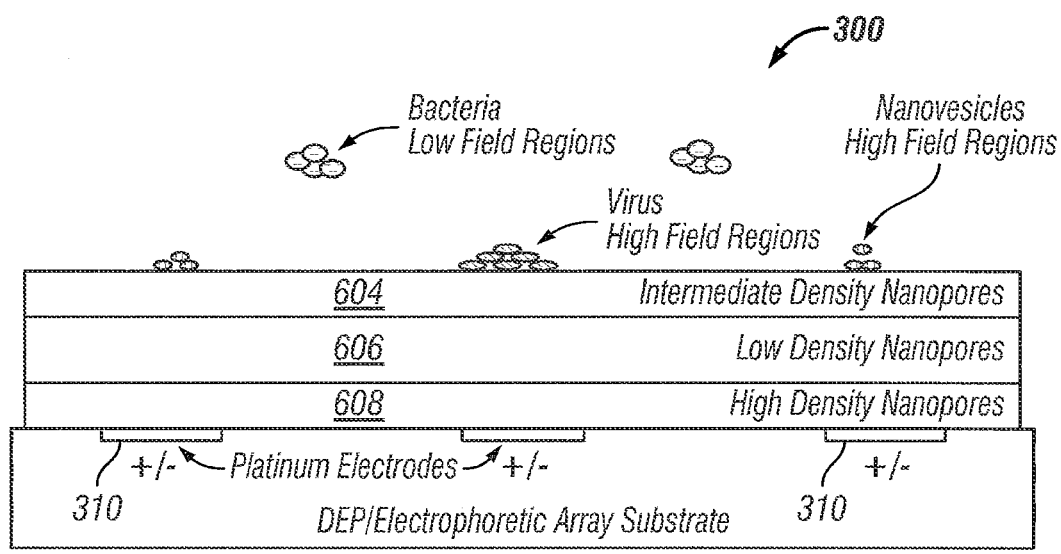
FIG. 16 shows the final pulsed AC DEP for separation of bacteria, virus and nanovesicles on the middle array section of the device.

FIG. 16 shows the enlarged view of the electrode array with the final pulsed AC DEP for separation of bacteria, virus and nanovesicles on the middle array section 404 of the device 300. Again, it should be kept in mind that this separation process on the middle array section can be run concurrently with, and independently of, other separation processes that are occurring on the other array sub-sections; e.g., DNA fragment separations can take place on the upper array section and cell separations can take place simultaneously on the other (lower) array sections.

Lastly, the parallel multiplexed electrode array can be used in conjunction with hierarchical cell sorting to create defined areas within the rows of electrodes where specific particles that are similar in size but have different dielectric properties can be trapped. A variety of diagnostic and therapeutic applications which can utilize electrokinetic, dielectrophoretic, electrophoretic and fluidic forces and effects all in conjunction with each other to increase separation sensitivity and efficiency in a device. Most importantly, these high performance and clinically useful separation processes are achieved only when the electrokinetic, electrophoretic and fluidic forces and effects are uniquely combined on a properly scaled and controlled electrode array device. In addition to this type of separation, dielectrophoresis, which is a lossless, potentially label less, parallel separation method, can be used in conjunction with more traditional separation methods which have far more sample preparation involved as well as greater loss of the sample, such as field flow fractionation, fluorescence assisted cell sorting (FACS) or magnetic assisted cell sorting, to achieve even greater levels of cell and nanoparticle separation for use in applications.

With regard to other aspects in the illustrated embodiments, it should be pointed out that when labeling (optical fluorescent, luminescent, electrochemical, magnetic, etc.) is added to the cells, nanoparticles, and biomarkers to be separated, the multiplexing described herein would likely be even more effective due to the labels helping to affect the size, conductivity and detectability of the entities.

Presently, the DEP separation mechanisms described above are in an early experimental data stage. A prototype system has been constructed, utilizing an electrode array structure as described above that receives biological materials for separation, that include cells, nanoparticles and hmw-DNA. Selective energizing of subsets of electrodes in the array structure has now been achieved with a function generator operating under control of suitable software programming, which can execute on conventional computers such as desktop or workstation computers. Individual electrodes can be controlled using this apparatus. The prototype system has an associated epifluorescent microscope for monitoring and recording the separation experiments (see Experimental Section below for additional description).

A variety of separation and isolation applications which include rare cell detection for adult stem cell isolation from blood, other bodily fluids or any buffers, e.g. hematopoietic progenitors; gross separation between cells, proteins and DNA/RNA fragments in blood, other bodily fluids or other buffers for the purposes of cancer detection and other diagnostics; cancer cell isolation from blood, other bodily fluids or other buffers for research, diagnostic as well as therapeutic purposes. Also envisioned are the uses for environmental monitoring and for the rapid detection of pathogens and bio-terror agents. Finally, also envisioned are systems, devices and techniques described in this invention can be used to separate, isolate and purify a variety of non-biological entities that include in addition to drug nanoparticles and nanovesicles; quantum dots, metallic nanoparticles, carbon nanotubes (CNTs), nanowires, and even micron and submicron CMOS devices and components; basically any macromolecule or nanocomponent that can be suspended or solubilized in an aqueous or mixed solvent system can be processed in the embodiments illustrated and using the techniques described herein. We also envision that these new devices will now allow directed self-assembly of DNA and other bioderivatized nanoparticles, nanocomponents, and mesoscale objects to be carried out. This can lead to new DNA genotyping and sequencing technologies ($1000 genome) and nano/micro bio/chemsensor applications, including highly integrated cell-sized "Fantastic Voyage" devices (inspired by the movie of the same name) that could be placed in the blood stream to carry out diagnostics, therapeutic delivery in-vitro microsurgery, i.e., remove clots and plaques, repair atherosclerotic arteries, etc.; as well as nanoelectronic, nanophotonic, photovoltaic, fuel cell, batteries, nanomaterials, and numerous other heterogeneous integration applications.

Using the devices and techniques described herein, a "sample to answer" result can be provided, wherein the separation operation results in holding at least one type of biological material at one of the electrode subsections, while the remainder of the sample fluid is washed from the device, so that a reagent into the sample processing device, followed by reacting the introduced reagent with the held type of biological material in the sample processing device. As noted above, the reagent may comprise a fluorescent die, antibodies, or the like. The sample-to-answer process may be used to perform a variety of tasks as described above, including PCR operations and the like.

The invention has been described above in terms of presently preferred embodiments so that an understanding of the present invention can be conveyed. There are, however, many configurations and permutations of the devices, system and separation mechanisms not specifically described herein, but to which the present invention is applicable. The present invention should therefore not be seen as limited to the particular embodiments described herein, but rather, it should be understood that the present invention has wide applicability with respect to biological separation systems generally. All modifications, variations, or equivalent arrangements and implementations that are within the scope of the attached claims should therefore be considered within the scope of the invention.

EXPERIMENTAL SECTION

Buffers and Conductivity Measurements

Concentrated 5× Tris Borate EDTA (TBE) buffer solution was obtained from USB Corporation (USB, Cleveland, Ohio, USA), and was diluted using deionized Milli-Q Ultrapure water (55 nS/cm) to the following concentrations: 0.01×TBE, 0.1×TBE and 1×TBE. Dulbecco's Phosphate Buffer Saline (1×PBS) solution was obtained from Invitrogen (Invitrogen, Carlsbad, Calif., USA) and was diluted using Milli-Q water to 0.1×PBS. Conductivity measurements were made with an Accumet Research AR-50 Conductivity meter (Fisher Scientific, Fair Lawn, N.J., USA) using a 2 cell (range: 10-2000 µS) and a 4 cell (range: 1-200 mS) electrode and was adjusted with proper conductivity standards. The following buffer conductivities were measured: 0.01×TBE—18.1 µS/cm; 0.1× TBE—125 µS/cm; 1×TBE—1.09 mS/cm; 0.1×PBS—1.77 mS/cm; and 1×PBS—16.8 mS/cm.

Particles, Nanoparticles and DNA Derivatization

Fluorescent polystyrene nanoparticles (FluoSpheres) with NeutrAvidin coated surfaces were purchased from Invitrogen (Invitrogen, San Diego, Calif., USA). The nanoparticle diameters were 0.04 µm (40 nm) and 0.2 µm (200 nm). The 40 nm polystyrene nanoparticles were red fluorescent (ex:585/em: 605) and the 200 nm polystyrene nanoparticles were yellow-green fluorescent (ex:505/em:515). Larger 10.14 µm carboxylated polystyrene particles were obtained from Bangs Labs (Bangs Labs, Fishers, Ind., USA). Biotinylated DNA oligonucleotide sequences were obtained from Trilink Bio Technologies (Trilink, San Diego, Calif., USA). The single-stranded 51 mer DNA oligonucleotide used to derivatize the 40 nm nanoparticles had the sequence—[5]'-Biotin-TCA GGG CCT CAC CAC CTA CTT CAT CCA CGT TCA CTC AGG GCC TCA CCA CCT [3]'. A second single-stranded 23 mer DNA oligonucleotide used had the sequence—[5]'-Biotin-GTA CGG CTG TCA TCA CTT AGA CC [3]'. The derivatization of the 40 nm NeutrAvidin nanoparticles with the biotinylated DNA oligonucleotides was carried out by first suspending the nanoparticles in different concentrations of Tris Borate EDTA (0.01×, 0.1×, 1×TBE) or Phosphate Buffered Saline (0.1×, 1×PBS) buffers. The ss-DNA oligonucleotide was added to the mixtures in the amounts of 400:1 (DNA:40 nm nanoparticles) ratio for the 51 mer ss-DNA sequence, and 6500:1 (DNA:40 nm nanoparticle) ratio for the 23 mer ss-DNA sequence. Once the DNA was added, the solution was vortexed at high speed for 20 seconds and then allowed to react for about 20 minutes. For the 40 nm DNA derivatized nanoparticle experiments, the DNA nanoparticle mixture was made by adding 0.5 µL of the stock solution into 299 µL of the appropriate buffer. For the 200 nm nanoparticle experiments, 0.5 µL of the stock solution was added to 299 µL of the appropriate buffer. Finally, 1 µL of the 10.14 µm polystyrene particle stock solution was added to the samples, the samples were then slowly mixed for about 10 seconds. The samples were now ready to be applied to the microarray cartridge device.

DEP Microelectrode Array Device

The microelectrode array devices used for these studies were obtained from Nanogen (San Diego, Calif., USA, NanoChip® 100 Cartridges). The circular microelectrodes on the array are 80 µm in diameter and made of platinum. The microarray is over-coated with 10 µm thick porous polyacrylamide hydrogel layer. The microarrays are enclosed in a microfluidic cartridge which forms a 20 µL sample chamber over the array that is covered with a glass window. Electrical connections to each individual microelectrode are pinned out to the bottom of the cartridge. Only a 3×3 subset of nine microelectrodes was used to carry out DEP. Alternating current (AC) electric fields were applied to the nine microelectrodes in a checkerboard addressing pattern. In this checkerboard pattern of addressing, each microelectrode has the opposite bias of its nearest neighbor. The corresponding computer model for the asymmetric electric field distribution created by this pattern has been discussed previously [27]. This model indicates that the positive DEP field maxima (high field regions) exist at (on) the microelectrodes and the negative DEP field minima (low field regions) exist in the areas between the electrodes. In general, for DEP in low conductance solutions the 60 nm DNA and 200 nm nanoparticles are expected to concentrate in the positive or high field regions over the microelectrodes [28] and the 10 micron particles concentrate in the negative or low field DEP regions [29] between the microelectrodes. The computations from the previous model were performed for a 5×5 microelectrode set [27]. Before each experiment, the microarray cartridge is flushed 10 times with 200 µL of the appropriate buffer, over a span of 5 minutes. The cartridge is allowed to sit for 5 minutes, and is then washed two more times with 200 µL of buffer. A total of 150 µL of the sample solution containing the nanoparticle mixture is then slowly injected into the cartridge, a final sample volume of about 20 μL remains in the cartridge.

Experimental Setup, Measurements, Fluorescence and SEM Analysis

The microarray devices were controlled using a custom made switching system (designed and constructed in our lab) that allows for individual control over the voltage being applied to each of the 100 microelectrodes. The microelectrodes were set to the proper AC frequency and voltages using an Agilent 33120A Arbitrary Function Generator (Agilent, Santa Clara, Calif., USA). AC frequencies ranged from 1000 Hz to 10,000 Hz, at 10 volts peak to peak (pk-pk). The wave form used for all experiments was sinusoidal. The experiments were visualized using a 10×PL Fluotar objective in a JenaLumar epifluorescent microscope (Zeiss, Jena, Germany) employing the appropriate excitation and emission filters (green fluorescence Ex 505 nm, Em 515 nm; red fluorescence Ex 585 nm, Em 605 nm. Both back lighted and the fluorescent images were captured using an Optronics 24-bit RGB CCD camera (Optronics, Goleta, Calif., USA). The image data was processed using a Canopus ADVC-55 video capture card (Canopus, San Jose, Calif., USA) connected to a laptop computer using either Adobe Premiere Pro (Adobe Systems Inc, San Jose, Calif., USA) or Windows Movie Maker. The final fluorescence data was analyzed by inputting individual fluorescent image frames of the video into MATLAB (Mathworks, Natick, Mass., USA) at 0 minutes, 30 seconds, 1 minute, 2 minutes, 4 minutes, 8 minutes, 16 minutes, and 20 minutes time points. The graphs were created using Excel from data gathered through MATLAB analysis of fluorescence intensity readings across the microelectrode. was created using MATLAB. The following data was used to create the graph: $\sigma_p$ (for 200 nm)=18 mS, $\sigma_p$ (for 40 nm+DNA)=50 mS $K_s$=0.9 nS, $\epsilon_p$=2.55$\epsilon_0$. r=30 nm & r=100 nm. f=3 kHz. After the conclusion of the DEP experiments the FCOS microarrays had all the fluid removed from their surface and were visualized using a Phillips XL30 scanning electron microscope (SEM). The SEM was used to image the final nanoparticle layers on the surface of the microarray.

References cited in this description comprise the following:

1. Tong, Y-K.; Lo, Y. M. D. Diagnostic developments involving cell-free (circulating) nucleic acids. Clinica Chimica Acta. 363:187-96; 2006.
2. Becker, F. F.; Wang, X-B.; Huang, Y.; Pethig, R.; Vykoukalt, Y.; Gascoyne, P. R. C. The removal of human leukemia cells from blood using interdigitated microelectrodes. J. Phys. D: Appl. Phys. 27:2659-2662; 1994.
3. Becker, F. F.; Wang, X-B.; Huang, Y.; Pethig, R.; Vykoukalt, Y.; Gascoyne, P. R. C. Separation of Human Breast Cancer Cells From Blood by Differential Dielectric Affinity. Proceedings of the National Academy of Sciences, 92:860-864; 1995.
4. Stephens M, Talary M S, Pethig R, Burett A K, Mils K I. The dielectrophoresis enrichment of CD34+ cells from peripheral blood stem cell harvests. Bone Marrow Transplant. 18:777-82. 1996.
5. Washizu, M.; Kurosawa, O. Electrostatic manipulation of DNA in microfabricated structures. Industry Applications, IEEE Transactions on. 26:1165-1172; 1990.
6. Washizu, M.; Kurosawa, O.; Arai, I.; Suzuki, S.; Shimamoto, N Applications of electrostatic stretch-and-positioning of DNA. Industry Applications, IEEE Transactions on. 31:447-456; 1995.
7. Asbury, C L; Van Den Engh, G. Trapping of DNA in Nonuniform Oscillating Electric Fields. Biophys J. 74:1024-1030; 1998.
8. Asbury, C L; Diercks, A. H.; Van Den Engh, G. Trapping of DNA by dielectrophoresis. Electrophoresis. 23:2658-2666; 2002.
9. Holzel, R.; Calander, N.; Chiragwandi, Z; Wil ander, M.; Bier, F. F. Trapping Single Molecules by Dielectrophoresis. Phys. Rev. Lett. 95:128102 (2005).
10. Ramos, A.; Morgan, H.; Green, N. G.; Castellanos, A. Ac electrokinetics: a review of forces in microelectrode structures. J. Phys. D: Appl. Phys. 31:2338-2353; 1998.
11. Goodard W. A., Brenner, D. W.; Lyshevski, S. B.; Iafrate, G. J.; Handbook of Nanoscience, $2^{nd}$ edition, ch 16, p5-8.
12. HiguGhi Yo, GhrQIDQsomalDNA fragmentation inapoptosis and necrosis induced by oxidative stress. Biochem Pharacol. 66:1527-35. 2003
13. Ziegler A, Zangemeister-Wittke D, Stahel R A. Circulating DNA: a new diagnostic gold mine? Cancer Treat Rev. 5:255-71. 2002.
14. Wu T L, Zhang D, Chia J H, Tsao K H, Sun C F, Wu J T. Cell-free DNA: measurement in varous carcinomas and establishment of normal reference range. Clin ChimActa. 21:77-87. 2002.
15. Higuchi Y.; Matsukawa S. Appearance of 1-2 Mbp giant DNA fragments as an early common response leading to cell death induced by various substances that cause oxidative stress. Free Radical Biology & Medicine, 23:90-99, 1997 23.
16. Gautschi 0, Bigosch C, Huegli B, Jerman $M_1$ Mar A, Chasse E, Ratschiler D, Weder W, Joerger M, Betticher D C, Stahel R $A_1$ Ziegler A. Circulating deoxyrbonucleic Acid as prognostic marker in non-small-cell lung cancer patients undergoing chemotherapy. J Clin Oneol. 22:4157-64. 2004.
17. Stroun $M_1$ Aner $P_1$ Lyautey J, et al_. Isolation and characterization of DNA from the plasma of cancer patients. Eur J Cancer Clin Oneol 23:707-712. 1987.
18. Morgan, H.; Hughes, M. P.; Green, N. G. "Separation of Sub micron Bioparticles by Dielectrophoresis" Biophysical Journal. 77:516-525. 1999.
19. Green, N. G.; Ramos, A.; Morgan, H. Ac electrokinetics: a survey of sub-micrometer particle dynamics. J. Phys. D: Appl. Phys. 33:632-641; 2000.
20. Tuukanen, S.; Toppar, J. J.; Kuzyk, A.; Hirviniemi, L; Hytonen, V. P.; Ilalainen T.; Torma, P. Carbon nanotubes as electrodes for dielectrophoresis of DNA. Nano Letters. 6:1339-1343; 2006.
21. Ching 1. et al., "Isolation of Cultured Cerivcal Carcinoma Cells Mixed with Peripheral Blood Cells on a Bioelectronic Chip", Analytical Chemistry, VoL. 70, #11, pp. 2321-2326, 1998.
22. Cheng, J. et al., "Preparation and Hybridization Analysis of DNA/A from E. coli on 15 Microfabricated Bioelectronic Chips", Nature Biotechnology, VoL. 16, pp. 541-546, 1998.
23. Huang Y, Ewalt K L, Tirado M, Haigis R, Forster A, Ackley D, Heller M J, O'Connell J P, and Krhak M, "Electric Manipulation of Bioparides and Macromolecules on Microfabricated Electrodes", Analytical Chemistry 2001, (73): 1549-59.
24. Huang $Y_1$ Joo S, Duhon M, Heller M J, Wallace B and Xu, "Dielectrophoretic Cell Separation 20 and Gene Expression Profiling on Microelectronic Chip Arrays", Analytical Chem. 2002, 74, 3362-71.
25. U.S. Pat. No. 5,632,957, May 27, 1997, Heller et al., Molecular Biological System Including Electrodes.
26. U.S. Pat. No. 6,289,590 B1 Aug. 28, 2001, Cheng et al., Chanell-Less Separation of 25 Bioparicles on a Bioelectronic Chip by Dielectrophoresis.
27. U.S. Pat. No. 6,403,367 B1, Jun. 11, 2002, Cheng et al., Integrated Portable Biological System. 24.

We claim:

1. A process for separating elutable nanoscale analytes from larger entities in a high conductance sample, the process comprising:
(a) applying a high conductance biological sample of >100 mS/m comprising whole blood, serum, plasma, urine or saliva, to an alternating current (AC) electrokinetic device comprising a plurality of non-sputtered alternating current (AC) electrodes; and
(b) with an alternating current, selectively energizing the electrodes and establishing dielectrophoretic (DEP) high field and dielectrophoretic (DEP) low field regions in the high conductance sample, whereby AC electrokinetic effects separate elutable nanoscale analytes from larger entities in the high conductance sample by isolating elutable nanoscale analytes in the dielectrophoretic (DEP) high field region and isolating larger entities in the dielectrophoretic (DEP) low field region.

2. The process of claim 1, wherein the alternating current has a frequency of less than 20 kHz.

3. The process of claim 1, wherein the alternating current has a frequency of 10-50 kHz.

4. The process of claim 1, wherein the nanoscale analytes: (1) are particles having a size of between 5 nm and 500 nm; (2) comprise (i) high molecular weight DNA, (ii) RNA, (iii) proteins, and/or (iv) cellular membrane; or (3) both.

5. The process of claim 1, wherein the larger entities comprise cells and micron-sized particles.

6. The process of claim 1, wherein the alternating current (AC) electrodes are solid platinum, palladium or gold materials.

7. The process of claim 1, wherein the alternating current (AC) electrodes are wires or rods.

8. The process of claim 1, further comprising removing the nanoscale analytes for further testing and storage.

9. The process of claim 1, further comprising monitoring a separation process and analysis of separated biological components.

10. The process of claim 1, further comprising selectively energizing the electrodes with direct current (DC) to establish DC electrophoretic fields, whereby DC electrokinetic effects provide for further separation of the elutable nanoscale analytes using DC electrophoresis.

* * * * *

UNITED STATES PATENT AND TRADEMARK OFFICE
CERTIFICATE OF CORRECTION

| | | |
|---|---|---|
| PATENT NO. | : 8,932,447 B2 | Page 1 of 1 |
| APPLICATION NO. | : 14/063884 | |
| DATED | : January 13, 2015 | |
| INVENTOR(S) | : Michael Heller et al. | |

It is certified that error appears in the above-identified patent and that said Letters Patent is hereby corrected as shown below:

In the Specification

STATEMENT AS TO RIGHTS TO INVENTIONS MADE UNDER FEDERALLY SPONSORED RESEARCH AND DEVELOPMENT section, Column 1, Lines 23-25, delete:
"This work was supported by NIH Grant/Contract CA119335. The Government of the United States of America may have certain rights in this invention."
And insert:
--This invention was made with government support under CA119335 awarded by the National Institutes of Health. The government has certain rights in the invention.--

Signed and Sealed this
Third Day of February, 2026

John A. Squires
*Director of the United States Patent and Trademark Office*

SEQUENCE LISTING

<160> NUMBER OF SEQ ID NOS: 2

<210> SEQ ID NO 1
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 1
tcagggcctc accacctact tcatccacgt tcactcaggg cctcaccacc t    51

<210> SEQ ID NO 2
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 2
gtacggctgt catcacttag acc    23